(12) United States Patent
Jon et al.

(10) Patent No.: US 11,904,019 B2
(45) Date of Patent: Feb. 20, 2024

(54) BILIRUBIN NANOPARTICLE, USE THEREOF, AND PREPARATION METHOD THEREFOR

(71) Applicant: Bilix Co., Ltd., Seoul (KR)

(72) Inventors: Sang Yong Jon, Daejeon (KR); Yong Hyun Lee, Daejeon (KR)

(73) Assignee: BILIX CO., LTD., Seoul (KR)

( * ) Notice: Subject to any disclaimer, the term of this patent is extended or adjusted under 35 U.S.C. 154(b) by 0 days.

(21) Appl. No.: 15/104,040

(22) PCT Filed: Dec. 26, 2014

(86) PCT No.: PCT/KR2014/012912
§ 371 (c)(1),
(2) Date: Jun. 13, 2016

(87) PCT Pub. No.: WO2015/099492
PCT Pub. Date: Jul. 2, 2015

(65) Prior Publication Data
US 2017/0028076 A1    Feb. 2, 2017

(30) Foreign Application Priority Data
Dec. 27, 2013 (KR) .......................... 10-2013-0165718

(51) Int. Cl.
| A61K 9/14 | (2006.01) |
| A61K 47/60 | (2017.01) |
| A61K 47/69 | (2017.01) |
| A61K 31/704 | (2006.01) |
| B82Y 5/00 | (2011.01) |

(52) U.S. Cl.
CPC ............ *A61K 47/60* (2017.08); *A61K 31/704* (2013.01); *A61K 47/6935* (2017.08); *B82Y 5/00* (2013.01)

(58) Field of Classification Search
None
See application file for complete search history.

(56) References Cited

U.S. PATENT DOCUMENTS

| 5,010,073 | A | * | 4/1991 | Kappas | .................. A61K 9/127 424/450 |
| 6,916,488 | B1 | | 7/2005 | Meier et al. | ................... 424/450 |
| 2004/0013717 | A1 | | 1/2004 | Allen et al. | ................... 424/450 |
| 2007/0015816 | A1 | | 1/2007 | Clark et al. | ................... 514/422 |

(Continued)

OTHER PUBLICATIONS

Boiadjiev et al., "pKa and Aggregation of Bilirubin: Titrimetric and Ultracentrifugation Studies on Water-Soluble Pegylated Conjugates of Bilirubin and Fatty Acids", Biochemistry, 43, 2004, pp. 15617-15632.*

(Continued)

*Primary Examiner* — Kevin S Orwig
(74) *Attorney, Agent, or Firm* — The PL Law Group, PLLC

(57) ABSTRACT

The present invention provides a bilirubin nanoparticle formed by the self-assembly of bilirubin and a composite comprising a hydrophilic polymer, a use thereof, and a preparation method therefor. The bilirubin nanoparticle according to the present invention can release a drug enclosed therein to the outside by being collapsed by light or active oxygen stimulation. The bilirubin nanoparticle according to the present invention exhibits antioxidant, antiangiogenic, anticancer, and anti-inflammatory activities.

16 Claims, 43 Drawing Sheets

(56) References Cited

U.S. PATENT DOCUMENTS

| | | | | |
|---|---|---|---|---|
| 2007/0032842 | A1* | 2/2007 | Strong | A61N 5/0621 607/88 |
| 2010/0196481 | A1* | 8/2010 | Pritchard | A61K 9/0024 424/487 |
| 2010/0291191 | A1* | 11/2010 | Shoichet | A61K 9/0024 424/450 |
| 2011/0022129 | A1 | 1/2011 | Prud'homme et al. | 607/88 |
| 2012/0070465 | A1* | 3/2012 | Takaishi | A61K 9/0004 424/400 |
| 2012/0301530 | A1* | 11/2012 | Uhlmann | A01N 59/16 424/405 |
| 2013/0345614 | A1 | 12/2013 | Mane | 604/6.08 |

OTHER PUBLICATIONS

Akiyoshi et al. "Self-Assembly of Hydrophobized Polysaccharide", Proc. Japan Acad. 1995, 17, pp. 15-19.*
Chung et al., "Chiral Recognition of Bilirubin by Polymeric Nanoparticles", Langmuir, 2002, 18, pp. 6462-6464.*
Stocker, R., et al. PNAS (1987), 84; pp. 8130-8134.*
Li, W., et al. Prog. Polym. Sci. (ePub Aug. 2012), 38; pp. 421-444.*
Singh, S., et al. Indian J. Sci. Technol. (2011), 4(3); pp. 177-180.*
Kynclova, E., et al. J. Mol. Recognit. (1996), 9; pp. 644-651 (Year: 1996).*
Salmaso, S., et al. J. Drug Del. (2013), Article ID 374252, 19 pgs.; http://dx.doi.org/10.1155/2013/374252 (Year: 2013).*
PubChem listing for bilirubin titaurine; accessed online Nov. 25, 2019 at https://pubchem.ncbi.nlm.nih.gov/compound/Bilirubin-ditaurine.*
PubChem listing for bilirubin diglucuronide; accessed online Nov. 25, 2019 at https://pubchem.ncbi.nlm.nih.gov/compound / Bilirubin-diglucuronide.*
Gura, T. Science (1997), 278(5340); 1041-1042.*
Kamb, A. Nat. Rev. Drug Discov. (2005), 4(2); 161-165.*
Roberts, T. G., et al. JAMA. (2004), 292(17); 2130-2140.*
Trivedi, R., et al. Nanomedicine (2010), 5(3); 485-505.*
MassiveBio; https://massivebio.com/advanced-stage-pancreatic-cancer; Jun. 3, 2020; accessed online Sep. 7, 2021.*
American Society of Clinical Oncology (ASCO) https://ascopost.com /News/59926; Apr. 11, 2019; accessed online Sep. 7, 2021.*
Protonterapia; https://www.protonterapia.eu/en/proton-therapy/treatment-spectrum/; May 31, 2011; accessed online Sep. 27, 2021.*
Pan, S.-T., et al. Clin. Exp. Pharmacol. Physiol. (2016), 43(8); 723-737.*
International Search Report (ISR) in PCT/KR2014/012912, dated Mar. 23, 2015 Qublished in WO 2015/099492.

Pashkovskaya, A. et al., (2009). "Light-triggered liposomal release: membrane germeabilization by ghotodxnamic action". *Langmuir* 26(8):5726-5733.
Stefan E. Boiadjiev et al., pKa and Aggregation of Bilirubin: Titrimetric and Ultracentrifugation Studies on Water-Soluble Pegylated Conjugates of Bilirubin and Fatty Acids, Biochemistry 2004, 43, pp. 15617-15632, Revised Manuscript Received Sep. 17, 2004.
Bioadjiev et al., "pKa and aggregation of bilirubin: titrimetric and ultracentrifugation studies on water-soluble pegylated conjugates of bilirubin and fatty acids," Biochemistry, 43:15617-15632 (2004).
Kim et al, "Bilibrubin nanoparticle preconditioning protects against hepatic ischemia-reperfusion injury," Biomaterials, 133:1-10 (2017).
Kim et al., "Bilirubin nanoparticles ameliorate alergic lung inflammation in a mouse model of asthma," Biomaterials, 140:37-44 (2017).
Kim et al., "PEGylated bilirubin nanoprticle as an anti-oxidative and anti-inflammatory demulcent in pancreatic islet xenotransplantation," Biomaterials, 133:242-252 (2017).
Lee et al., "Bilirubin nanoparticle-assisted delivery of small molecule-drug conjugate for targeted cancer therapy," Biomacromolecules, 19:2270-2277 (2018).
Lee et al., "Bilirubin nanoparticles as a nanomedicine for anti-inflammation therapy," Angew Chem Int Ed, 55:7460-7463 (2016).
Lee et al., "Biotinylated bilirubin nanoparticles as a tumor microenvironment-responsive drug delivery system for target cancer therapy," Adv Sci, 1-8 (2018).
Lee et al., "Multistimuli-responsive bilirubin nanoparticles for anticancer therapy," Angew Chem Int Ed, 55:1-6 (2016).
Ollinger et al., "Bilirubin and biliverdin treatment of atherosclerotic diseases," Cell Cycle, 6(1):39-42 (2007).
Ollinger et al., "Therapeutic applications of bilirubin and biliverdin in transplantation," Antioxidants & Redox Signaling, 9(12):2175-2185 (2007).
Yanjiao Han et al. "Zwitterlation mitigates protein bioactivity loss in vitro over PEGylation" Chemical Science, vol. 9, pp. 8561-8566, 2018.
Richard B. Greenwald et al., "Highly Water Soluble Taxol Derivatives: 7-Polyethylene Glycol Carbamates and Carbonates", J. Org. Chem., vol. 60, pp. 331-336, 1995.
Swaroop Mishra et al., "PEGylation significantly affects cellular uptake and intracellular trafficking of non-viral gene delivery particles", Eur. J. Cell Biol., vol. 83, pp. 97-111, 2004.
Stefaan J. Soenen et al. "The Cellular Interactions of PEGylated Gold Nanoparticles: Effect of PEGylation on Cellular Uptake and Cytotoxicity" Particle & Particle System Characterization, vol. 31, pp. 794-800, 2014.
Francesco M. Veronese et al., "The Impact of PEGylation on Biological Therapies", Biodrugs, vol. 22 (5), pp. 315-329, 2008.

* cited by examiner

Colitis Model Group  Normal Group

BILIRUBIN NANOPARTICLE, USE THEREOF, AND PREPARATION METHOD THEREFOR

CROSS-REFERENCE TO RELATED APPLICATIONS

This application is a national phase application of PCT Application No. PCT/KR2014/012912, filed on Dec. 26, 2014, which claims the benefit and priority to Korean Patent Application No. 10-2013-0165718, filed Dec. 27, 2013. The entire disclosures of the applications identified in this paragraph are incorporated herein by references.

FIELD

The present invention relates to bilirubin nanoparticles, a use thereof, and a preparation method therefor.

BACKGROUND

With the rapid progress of nanotechnology over the past decade, there is growing interest in the polymeric biomaterials that can be disassembled upon an external or internal stimulus but otherwise are stable under physiological conditions. Various internal and external stimuli, such as pH, specific enzymes, temperature, ultrasound, reactive oxygen species, and light are being explored. Among them, an optical stimulus is especially attractive as it can be remotely applied for a short period of time with high spatial and temporal precision in a controlled fashion. In addition, abnormal levels of reactive oxygen species in inflammation sites are able to be used as an inflammation site specific triggering stimulus.

Further, there is growing interest in the therapy of diseases, such as inflammatory diseases, using nanoparticles. ROS are present at the outbreak site of an inflammatory disease, and are closely associated with the progress of the disease. Therefore, various therapeutic nanoparticles having an inflammatory effect were developed for the therapy of various diseases, such as cardiovascular disorders, stroke, and IBD. In addition, a cancer therapy method has been developed using nanoparticles having a photosensitizing effect. Furthermore, theragnosis capable of simultaneously performing imaging and therapy using nanoparticles is drawing attention as the optimal therapy measure through personalized medicine.

Bilirubin is a yellowish final metabolite formed from heme. This is bilirubin's structure and have many hydrophilic groups, but is very hydrophobic due to their intramolecular hydrogen bonding. Any organic solvents except chloroform and dimehtyl sulfoxide cannot dissolve bilirubin. Water also.

If it didn't happen for bilirubin to be metabolized in liver, bilirubin cannot be excreted and then, accumulated into our body such as skin. We call this phenomena as Jaundice. We can diagnose an abnormal liver's function in adult or liver's immaturity in neonate from jaundice. Unlike adult's jaundice, neonatal jaundice is harmful to newborn infant's brain because high level of bilirubin can hampen brain's development. In this situation, we can use phototherapy for decreasing bilirubin concentration in our body. Once light is exposured into our body, bilirubin can be photoisomerized, which results in the break of bilirubin's intramolecular hydrogen bonding and consequently, bilirubin can be hydrophilc photoisomer that can be excreted into bile or urine itself. Furthermore, bilirubin can generate reactive oxygen species from oxygen during phototherapy and then the reactive oxygen species can oxidize bilirubin into colorless oxidation products which can be excreted into urine itself.

Furthermore, bilirubin is a potent antioxidant. When bilirubin scavenge ROS, hydrophobic bilirubin can be oxidized into hydrophilic biliverdin which can be oxidized more into more hydrophilic compound.

Therefore, bilirubin has several very interesting properties, first is Photoisomerization properties. When exposured to the blue light, bilirubin can be photoisomerized, which results in the break of bilirubin's intramolecular hydrogen bonding and consequently, bilirubin can be hydrophilc photoisomer. Secondly, bilirubin has a photodynamic effect when stimulied by the more strong blue light which results in generating reactive oxygen species. In addition, bilirubin can emit fluorescence while bound to BSA. Finally, bilirubin has powerful antioxidant effects which can scavenge the reactive oxygen species including peroxy radical, hydrogen peroxide, hydroxy radical, and hypochlorous acid.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors searched and endeavored to develop nanoparticles that have fluorescent characteristics, photosensitizing characteristics, and antioxidative characteristics, and that respond to light or reactive oxygen species as stimuli. As a result, the present inventors formed a bilirubin self-assembly in the water system by introducing a hydrophilic block into hydrophobic bilirubin, and verified that the self assembly had: a drug encapsulating capacity, an antioxidative capacity, and an anti-angiogenic capacity; a reactive oxygen species generating capacity through the exposure to light; a drug release capacity through the disruption of the self-assembly caused by the exposure to light or reactive oxygen species; and anticancer and anti-inflammatory activities, and thus completed the present invention.

Accordingly, an aspect of the present invention is to provide bilirubin nanoparticles.

Another aspect of the present invention is to provide a pharmaceutical composition for preventing or treating a cancer.

Still another aspect of the present invention is to provide a method for treating a cancer.

Still another aspect of the present invention is to provide a pharmaceutical composition for preventing or treating an inflammatory disease.

Still another aspect of the present invention is to provide a method for treating an inflammatory disease.

Still another aspect of the present invention is to provide a pharmaceutical composition for preventing or treating an angiogenesis-related disease.

Still another aspect of the present invention is to provide a method for treating an angiogenesis-related disease.

Still another aspect of the present invention is to provide an antioxidative composition.

Still another aspect of the present invention is to provide a method for preparing bilirubin nanoparticles.

Other purposes and advantages of the present disclosure will become clarified by the following detailed description of invention, claims, and drawings.

Technical Solution

In accordance with an aspect of the present invention, there are provided a bilirubin nanoparticle formed by self-assembling of a composite containing bilirubin and a hydrophilic polymer bound to the bilirubin.

The present inventors searched and endeavored to develop nanoparticles that have fluorescent characteristics, photosensitizing characteristics, and antioxidative characteristics, and that respond to light or reactive oxygen species as stimuli. As a result, the present inventors formed a bilirubin self-assembly in the water system by introducing a hydrophilic block into hydrophobic bilirubin, and verified that the self-assembly had: a drug encapsulating capacity, an antioxidative capacity, and an anti-angiogenic capacity; a reactive oxygen species generating capacity due to the exposure to light; a drug release capacity through the disruption of the self-assembly caused by the exposure to light or reactive oxygen species; and anticancer and anti-inflammatory activities.

According to an embodiment of the present invention, the bilirubin nanoparticle of the present invention is formed by the self-assembling of a composite, which contains bilirubin and a hydrophilic polymer bound thereto, and may be formed by the self-assembling in the water system.

According to an embodiment of the present invention, the bilirubin nanoparticle has a size of 1-5,000 nm. In a specific embodiment, the size of the bilirubin nanoparticle is 50-1,000 nm, and 50-500 nm in another particular embodiment, and 50-300 nm in a still another particular embodiment.

According to an embodiment of the present invention, the bilirubin nanoparticle of the present invention encapsulates a cargo. A cargo of a hydrophilic material may be encapsulated inside the nanoparticle, and a cargo of a hydrophobic material may be integrated in a hydrophobic membrane formed by bilirubin. Therefore, the term "encapsulation" herein is used as a wide concept, including the integration of a cargo.

In a specific embodiment, the cargo is a drug. The drug includes hydrophilic drugs, hydrophobic drugs, chemical drugs, and bio-drugs. Examples of these drugs may be anti-cancer agents, antioxidants, anti-inflammatory agents, painkillers, anti-arthritic agents, sedatives, antidepressants, antipsychotics, tranquilizers, antianxiety agents, anti-angiogenic inhibitors, immunosuppressants, anti-viral agents, antibiotics, anorexigenic agent, antihistamines, hormone preparations, antithrombotic agents, diuretics, antihypertensive agents, cardiovascular therapeutic agents, vasodilators, and the like.

According to an embodiment of the present invention, the bilirubin nanoparticle of the present invention may scavenge reactive oxygen species. As verified in examples below, the bilirubin nanoparticles of the present invention can be selectively accumulated in an inflammatory tissue, and thus the bilirubin nanoparticles can be used in the treatment of inflammation by scavenging reactive oxygen species in the inflammatory tissue.

According to an embodiment of the present invention, the bilirubin nanoparticles of the present invention are disassembled or disrupted by light, thereby releasing the encapsulated cargo to the periphery thereof.

In a particular embodiment, when the nanoparticles of the present invention encapsulate an anticancer agent, the bilirubin nanoparticles may be selectively accumulated in the tumor tissue, and thus the nanoparticles are disassembled or disrupted by the light (e.g., blue-wavelength light) irradiated from the outside, thereby releasing the anticancer agent to the cancer tissue and obtaining a cancer treatment effect by the released anticancer agent.

According to an embodiment of the present invention, the bilirubin nanoparticles of the present invention may be disassembled or disrupted by 430 nm to 480 nm wavelength light.

According to another embodiment of the present invention, the bilirubin nanoparticles of the present invention may be disassembled or disrupted by 620 nm to 680 nm wavelength light.

According to an embodiment of the present invention, the bilirubin nanoparticles of the present invention are disassembled or disrupted by reactive oxygen species, thereby releasing the encapsulated cargo to the periphery thereof.

In a specific embodiment, the reactive oxygen species are ones present in an inflammatory site. Therefore, in cases where the nanoparticles of the present invention encapsulate an anticancer agent (or anti-inflammatory agent), the nanoparticles are disassembled or disrupted by the reactive oxygen species present in the cancer (or inflammation) site, thereby releasing the anticancer agent (or anti-inflammatory agent) and obtaining a cancer (inflammatory disease) treatment effect by the released anticancer agent (or anti-inflammatory agent).

According to an embodiment of the present invention, the bilirubin nanoparticles of the present invention may generate reactive oxygen species by light. Therefore, the bilirubin nanoparticles of the present invention can be selectively accumulated in the tumor tissue, and, thus, reactive oxygen species are generated by the light (e.g., blue wavelength light) irradiated from the outside, thereby obtaining a cancer treatment effect.

According to an embodiment of the present invention, the bilirubin nanoparticles of the present invention may exhibit an anti-angiogenic activity.

According to the present invention, the hydrophilic polymer binds to bilirubin to form a composite, which functions as a constituent component of the bilirubin nanoparticles. Since the bilirubin nanoparticles of the present invention are applied into the body, the hydrophilic polymer is preferably biocompatible.

Examples of the hydrophilic polymer usable in the present invention may include polyethylene glycol (PEG), poly(acrylic acid), poly(acrylate), poly(acrylamide), poly(vinyl ester), poly(vinyl alcohol), polystryene, polyoxide, cellulose, starch, polysaccharides, polyelectrolyte, poly(1-nitropropylene), poly(N-vinyl pyrrolidone), poly(vinyl amine), poly(beta-hydroxyethylmethacrylate), polyethyleneoxide, poly(ethylene oxide-b-propylene oxide), and polylysine.

Still another example of the hydrophilic polymer usable in the present invention may include collagen, chitosan, gelatin, acacia gum, dextran, fibrin, hyaluronic acid, pectin, agar, galactomannan, xanthan, and alginate.

Still another example of the hydrophilic polymer usable in the present invention may include a peptide composed of two or more (e.g., 2-50) amino acids. The amino acids may include natural amino acids and non-natural amino acids. The hydrophilic amino acids include glutamine, aspartic acid, glutamic acid, threonine, asparagine, arginine, serine, and the like, and the hydrophobic amino acids include phenylalanine, tryptophan, isoleucine, leucine, proline, methionine, valine, alanine, and the like. Examples of the non-coded hydrophilic amino acid may include Cit and hCys. A person skilled in the art could easily synthesize the hydrophilic peptides on the basis of this information and peptide synthesis techniques, thereby preparing bilirubin nanoparticles.

The hydrophilic polymer includes not only the above-mentioned polymers but also derivatives thereof.

According to an embodiment of the present invention, the hydrophilic polymer is a polyethylene glycol or a derivative thereof. Examples of the polyethylene glycol derivative may include methoxy polyethylene glycol (PEG), succinimide of PEG propionic acid, succinimide of PEG butanoic acid, branched PEG-NHS, PEG succinimidyl succinate, succinimide of carboxymethylated PEG, benzotriazole carbonate of PEG, PEG-glycidyl ether, PEG-oxycarbonylimidazole, PEG nitrophenyl carbonates, PEG-aldehyde, PEG succinimidyl carboxymethyl ester, and PEG succinimidyl ester.

According to an embodiment of the present invention, the hydrophilic polymer is bound to a carboxyl group of bilirubin to form an amphipathic composite.

According to an embodiment of the present invention, the hydrophilic polymer has an amine group at a side chain or a terminal end thereof.

In accordance with another aspect of the present invention, there is provided a pharmaceutical composition for preventing or treating a cancer, the pharmaceutical composition containing: (a) a pharmaceutically effective amount of the bilirubin nanoparticle of the present invention; and (b) a pharmaceutically acceptable carrier.

In accordance with still another aspect of the present invention, there is provided a method for treating a cancer, comprising administering the pharmaceutical composition to a subject.

The bilirubin nanoparticles of the present invention exhibit an anti-angiogenic activity, and thus can be used in the cancer prevention and treatment.

According to an embodiment of the present invention, the composition of the present invention is directed to a pharmaceutical composition for treating cancers through photo-stimulation (pharmaceutical composition for photodynamic therapy). The bilirubin nanoparticles of the present invention, as a carrier of photosensitive drugs having fluorescent and photodynamic effects, may be utilized in the cancer treatment. Specifically, when the anticancer-loaded bilirubin nanoparticles are parenterally administered into the body, the bilirubin nanoparticles are accumulated in the tumor tissue by an EPR effect. Here, when the light from the outside is irradiated to the tumor tissue, a hydrophobic layer of bilirubin is converted into a hydrophilic layer containing a hydrophilic photoisomer, thereby disassembling (disrupting) the nanoparticles, and, thus the anticancer drug contained in the nanoparticles is released to the tumor tissue, thereby allowing cancer treatment. At the same time, the monomers isolated from the nanoparticles bind to albumin, and thus fluorescence is released from the tumor tissue, thereby allowing the imaging of the tumor tissue using the fluorescence.

In addition, when irradiated by a stronger blue-wavelength light, the bilirubin nanoparticles of the present invention generate reactive oxygen species, thereby obtaining an anticancer effect even by the generated reactive oxygen species. Hence, the bilirubin nanoparticles, per se, of the present invention can be used in the photodynamic treatment.

Examples of the cancer to which the present invention can be applied may include colorectal cancer, pancreatic cancer, biliary tract cancer, neuroendocrine tumor, lung cancer, breast cancer, ovarian cancer, liver cancer, bronchial cancer, nasopharyngeal cancer, laryngeal cancer, stomach cancer, bladder cancer, colon cancer, cervical cancer, brain cancer, prostate cancer, bone cancer, head and neck cancer, skin cancer, thyroid cancer, parathyroid cancer, ureter cancer, and the like.

According to an embodiment of the present invention, the subject is a mammal including a human being.

According to an embodiment of the present invention, the bilirubin nanoparticles encapsulate an anticancer agent.

In accordance with another aspect of the present invention, there is provided a pharmaceutical composition for preventing or treating an inflammatory disease, the pharmaceutical composition containing: (a) a pharmaceutically effective amount of the bilirubin nanoparticle of the present invention; and (b) a pharmaceutically acceptable carrier.

In accordance with still another aspect of the present invention, there is provided a method for treating an inflammatory disease, comprising administering the pharmaceutical composition to a subject.

The bilirubin nanoparticles of the present invention may be utilized as an ROS-sensitive material for treating inflammatory diseases. Specifically, the anti-inflammatory drug-loaded bilirubin nanoparticles, which are parenterally administered into the body, can target the inflammatory site by an EPR effect. At the inflammation site, the nanoparticles can exhibit an anti-inflammatory activity by scavenging an abnormal level of reactive oxygen species. At the same time, the hydrophobic bilirubin is oxidized into a hydrophilic viliverdin oxide, and thus the nanoparticles are disassembled (or disrupted), or the bilirubin is degraded into smaller compounds through additional oxidation, and thus the nanoparticles are disassembled (or disrupted), so that the drug contained in the nanoparticles is released into the inflammatory site, thereby allowing the treatment of inflammation. In addition, the release of the drug from the nanoparticles may occur by the uptake of macrophagocytes.

According to an embodiment of the present invention, the bilirubin nanoparticles encapsulate a therapeutic agent for inflammatory diseases.

Examples of the inflammatory diseases, to which the present invention can be applied, may include inflammatory bowel disease, atopic dermatitis, edema, dermatitis, allergies, asthma, conjunctivitis, periodontitis, rhinitis, otitis media, atherosclerosis, pharyngolaryngitis, tonsillitis, pneumonia, gastric ulcers, gastritis, Crohn's disease, colitis, hemorrhoids, gout, ankylosing spondylitis, rheumatic fever, lupus, fibromyalgia, psoriatic arthritis, osteoarthritis, rheumatoid arthritis, Periarthritis of shoulde, tendinitis, tenosynovitis, myositis, hepatitis, cystitis, nephritis, Sjogren's syndrome, and multiple sclerosis.

According to an embodiment of the present invention, the bilirubin nanoparticles inhibit a myeloperoxidase (MPO) activity.

According to an embodiment of the present invention, the bilirubin nanoparticles reduce the levels of pro-inflammatory cytokines.

In accordance with another aspect of the present invention, there is provided a pharmaceutical composition for preventing or treating an angiogenesis-related disease, the pharmaceutical composition containing: (a) a pharmaceutically effective amount of the bilirubin nanoparticle of the present invention; and (b) a pharmaceutically acceptable carrier.

In accordance with still another aspect of the present invention, there is provided a method for treating an angiogenesis-related disease, comprising administering the pharmaceutical composition to a subject in need of treatment.

In accordance with still another aspect of the present invention, there is provided a method for treating an angiogenesis-related disease, comprising administering the pharmaceutical composition to a subject.

As used herein, the term "angiogenesis-related diseases" refers to diseases caused by angiogenesis of capillary vessels stretched in a manner in which vascular endothelial cells bud from the existing blood vessel and infiltrate into tissues.

According to an embodiment of the present invention, the angiogenesis-related disease is cancer, diabetic restinosis, age-related macular degeneration, rheumatoid arthritis, endometriosis, psoriasis, or chronic inflammation.

In accordance with still another aspect of the present invention, there is provided an antioxidative composition containing the bilirubin nanoparticle of the present invention.

According to an embodiment, the antioxidative composition of the present invention may be implemented as a pharmaceutical composition or a cosmetic composition.

As used herein, the term "pharmaceutically effective amount" refers to an amount that is sufficient to attain the above-described pharmaceutical effect.

Where the composition of this invention is prepared as a pharmaceutical composition, the pharmaceutical composition of this invention contains a pharmaceutically acceptable carrier. The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative.

The pharmaceutical composition of the present invention can be used through parenteral administration, which may be, for example, intravenous administration, intraperitoneal administration, intramuscular administration, subcutaneous administration, or local administration. Further, oral administration, rectal administration, inhalation administration, intranasal administration, or the like may be possible.

The appropriate dose of the pharmaceutical composition of the present invention varies depending on factors, such as the formulating method, manner of administration, patient's age, body weight, or gender, severity of disease, food, time of administration, route of administration, excretion rate, and response sensitivity, and an ordinarily skilled practitioner can easily judge and prescribe the dose effective for the desired treatment or prevention.

The pharmaceutical composition of the present invention is formulated using a pharmaceutically acceptable carrier and/or excipient, according to the method that is easily conducted by a person having ordinary skills in the art to which the present invention pertains, and the pharmaceutical composition may be prepared into a unit dosage form or may be inserted into a multidose container. Here, the dosage form may be a solution in an oily or aqueous medium, a suspension, or an emulsion, and may further include a dispersant or a stabilizer.

In accordance with still another aspect of the present invention, there is provided a method for preparing bilirubin nanoparticle, the method including: (a) preparing a bilirubin-hydrophilic polymer composite by binding a hydrophilic polymer to bilirubin; (b) dissolving the bilirubin-hydrophilic polymer composite in chloroform or dimethyl sulfoxide; (c) removing the chloroform or dimethyl sulfoxide to form a bilirubin-hydrophilic polymer composite film layer; and (d) treating the film layer with a hydrophilic solvent to self-assemble bilirubin nanoparticles.

The respective steps of the preparing method are shown in FIG. 4.

Advantageous Effects

The features and advantages of this invention will be summarized as follows:

(i) The present invention provides bilirubin nanoparticles formed by self-assembling of an amphipathic composite containing bilirubin and a hydrophilic polymer, a use thereof, and a preparing method therefor.

(ii) The bilirubin nanoparticles of the present invention are disassembled or disrupted by the stimulation of light or reactive oxygen species, thereby releasing the drug encapsulated therein to the outside.

(iii) The bilirubin nanoparticles of the present invention exhibit an antioxidative activity, an anti-angiogenic activity, an anticancer activity, and an anti-inflammatory activity.

(iv) The bilirubin nanoparticles of the present invention have fluorescence.

MODE FOR CARRYING OUT THE INVENTION

Figure 1:
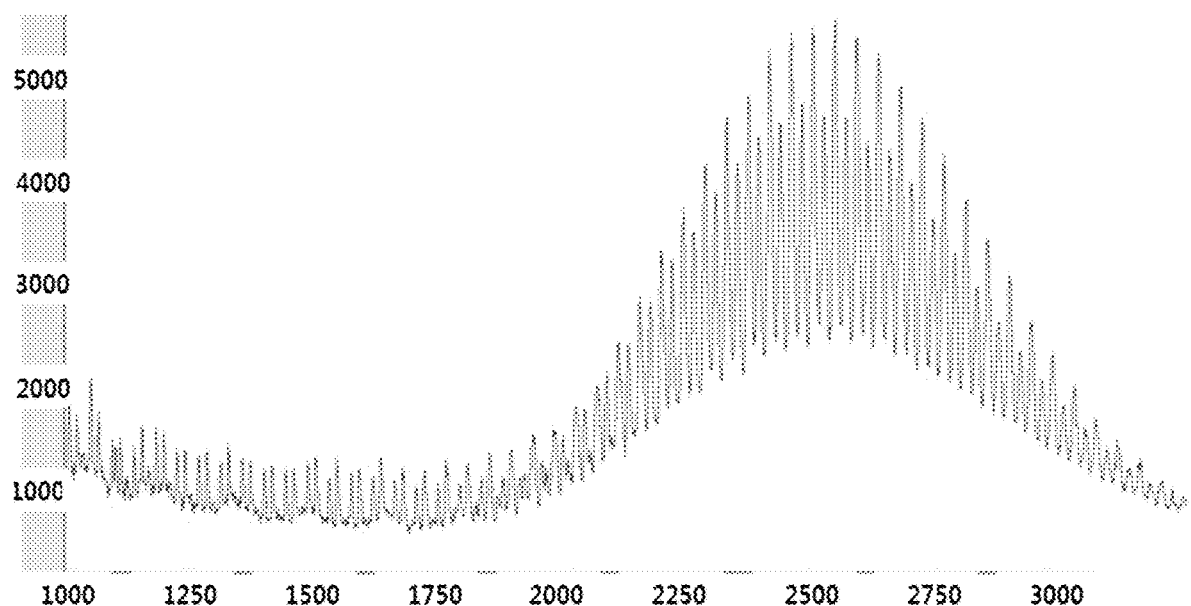
FIG. 1 shows MALDI-TOF results of PEG-BR.

The present invention will now be described in further detail by examples. It would be obvious to those skilled in the art that these examples are intended to be more concretely illustrative and the scope of the present invention as set forth in the appended claims is not limited to or by the examples.

EXAMPLES

Material and Method

PEGylated Bilirubin (PEG-BR) Synthesis

The Bilirubin and mPEG2,000-NH$_2$ were used for pegylation of bilirubin. Bilirubin (292 mg, 0.5 mmol) and EDC (95.5 mg, 0.6 mmol) was dissolved in the DMSO (5 ml). After stirring for 10 min at R.T, mPEG2000-NH$_2$ (400 mg, 0.2 mmol) and TEA (150 µl) were added to this mixture and then the reaction was allowed to stir for 4 hr at R.T under a nitrogen atmosphere. To remove free bilirubin, 45 ml of methanol was added to the reaction mixture and after centrifugation at 3,000 rpm for 10 min, precipitate was discarded and the supernatant was evaporated. Ether was added to the concentrated reaction mixture to make precipitate. The resulting precipitate was dissolved in chloroform for purification using column chromatography. After column chromatography on silica with chloroform/methanol (85:1 as mobile phase, the solvents were evaporated to yield PEGylated Bilirubin. The PEG-BR was analysed by $^1$H-NMR, UV and MALDI-TOF.

PEGylated Bilirubin Nanovesicles (BRNVs) Preparation

PEG-BR (5 mg) was dissolved in the chloroform (200 µl) and then dried under a stream of nitrogen gas and further dried under vacuum to make the film layer. Phosphate PBS (150 mM NaCl, 10 mM phosphate, pH 7.4) was added to the film layer for the formulation of nanoparticles. After sonication for 10 min, evenly size's PEGylated Bilirubin Nanoparticles (BRNVs) were acquired. Freshly prepared BRNVs were characterized by Dynamic light scattering (DLS) detection, zetapotential analysis, and visual evidence of particle formation was obtained via a transmission electron microscope (TEM) and a scanning electron microscope (SEM).

Critical Micelle Concentration of BRNVs

Nanoparticle critical vesicle concentration was measured. Briefly, the film layer formed from various amount of PEG-BR was prepared, and 1 ml of phosphate PBS (150 mM NaCl, 10 mM phosphate, pH 7.4) was added to the film layer for the formulation of nanoparticles. Nextly, nanoparticle formation in each group was determined by dynamic lightning scattering (DLS).

BRNVs Stability

To determine BRNVs's stability in R.T, BRNVs's size was measured by DLS zetasizer every day for 8 days.

Hydrogen Peroxide Scavenging Effect of BRNVs (Antioxidant Activity)

Quenching activities of hydrogen peroxide were quantified using EnzyChrom™ Catalase Assay Kit (MEDIBENA Life Science & Diagnostic Solutions). Briefly, hydrogen peroxide (50 µM, 90 µl) was treated with different concentrations of BRNVs (10 µl). After incubation for 30 min, remaining concentrations of the hydrogen peroxide in each group were determined by incubating each sample with a 100 µl of HRP/Dye detection reagent for 10 min and then checking fluorescence intensity ($\lambda$em/ex=585/530 nm).

ROS and Light-Responsive Disruption of BRNVs

BRNVs disruption in response to peroxy radical was examined. BRNVs (45 µg/mL) in DPBS were incubated with a 100 mM of peroxy radical generating reagent, 2,2'-azobis (2-amidinopropane) dihydrochloride (AAPH), at 37°

C. The UV/VIS spectra or size of BRNVs upon exposure of various concentrations of peroxy radicals were monitored by UV/Vis spectrometer or DLS at predetermined time (0, 10, 60 min). The reaction was also monitored at 37° C. in a spectrophotometer by measuring the absorbance at 453 and 650 nm in the spectrophotometer.

Drug Encapsulation

For hydrophilic drugs (DOX) loading, 3 mg of PEG-BR film layer was hydrated with 300 μg of doxorubicin (DOX) and phosphate PBS (150 mM NaCl, 10 mM phosphate, pH 7.4). After sonication for 10 min and incubation for 2 h at 30° C., free DOX was removed by gel filtration using a Sephadex CL-4B column (Sigma-aldrich) equilibrated with 20 mM HEPES-buffered 5% glucose (HBG). A total of 20 2-ml fractions were collected and for each fraction, each solution was dried under freeze-dried and then 200 μl of acetonitrile was added to the residues. Doxorubicin fluorescence in each fraction was then measured with a fluorometer.

For hydrophobic drugs (Docetaxel, DTX) loading, 400 μg of DTX and a 3 mg of PEG-BR were dissolved in chloroform, and then dried under a stream of nitrogen gas and further dried under vacuum to make the film layer composing of PEG-BR and DTX. The film layer was hydrated by Phosphate PBS (150 mM NaCl, 10 mM phosphate, pH 7.4). Free DTX was easily eliminated by precipitation method using centrifugation (8,000 rpm, 5 min) and filter method using a membrane filter (0.45 μm), and then the supernatant containing BRNVs loaded with DTX was used. To determine the loading amount of DTX in BRNVs loaded with DTX (DTX/BRNVs), 100 μl of BRNVs suspension loaded with DTX was lyophilized and 100 μl of ACN was added to this residues, and then filtered through a membrane filter (0.45 μm). The concentration of DTX in a 10 μL portion of the filtrate was determined by HPLC.

The encapsulation efficiency and the drug loading efficiency were calculated from the following equations:

Encapsulation efficiency(%)=weight of drug in BRNVs/weight of drug fed Initially×100%   Equation 1

Drug loading efficiency(%)=weight of drug in BRNVs/(weight of drug in vesicle+weight of PEG-BR fed initially)×100%   Equation 2

Drug Release by a Light Exposure

The release of integrated drug (DTX) from DTX/BRNVs was performed in

PBS buffer using extraction method. For measuring the drug release profile, DTX/BRNVs (1 mg/ml, 10% DTX loading percentage) were split equally into 4 microtubes. These microtubes were irradiated with 450 nm of light (10 mW/cm$^2$, 10 hz) or 650 nm of light (80 mW/cm$^2$). At each time point (0, 1, 5 and 10 min), one of 4 microtubes was taken and extracted with same volume of chloroform for 10 s and then was lyophilized and 100 μl of ACN was added to this residues and then, filtered through a membrane filter (0.45 μm). The concentration of DTX in a 10 μL portion of the filtrate was determined by HPLC.

The release of encapsulated drug (DOX) from DOX-loading BRNVs (DOX@BRNVs) by light stimulus was performed in PBS buffer at 37° C. For measuring the drug release profile, DOX@BRNVs (1 mg/ml, 10% DOX loading percentage) were prepared. DOX@BRNVs were irradiated with 450 nm of light (10 mW/cm$^2$, 10 hz) or 650 nm of light (80 mW/cm$^2$). At each time point (0, 1, 5 and 10 min), the amount of DOX released in the resulting solution was monitored by fluorescence emission at $\lambda_{max}$ 550 nm with excitation at 480 nm.

BRNVs's Fluorescence Measurement

BRNVs solutions (2 mg/ml) with or without 0.5% Triton-X were prepared and loaded on 96-well black plate. Emission spectra were recorded with a fluoromax fluorometer. The solutions were excited at 450 nm and emission was measured and integrated from 530 nm to 800 nm (cut off: 515 nm). The solutions were excited at 650 nm and emission was measured and integrated from 680 to 800 nm. (cut off: 690 nm)

Cell Culture

Mammalian CHO-K1 cells were cultured in RPMI1940 medium with 10% (v/v) heat-inactivated fetal bovine serum (FBS), 100 IU/ml penicillin and L-glutamine in a humidified 5% $CO_2$ atmosphere at 37° C., and A549 cells were incubated in Ham's F-12K medium supplemented with 10% FBS in a humidified 5% $CO_2$ atmosphere at 37° C. Endothelial cell line human vascular endothelial cells (HUVECs) were cultured in EGM2 medium (Lonza) in a humidified 5% $CO_2$ atmosphere at 37° C.

Confocal Microscopy

Confocal microscopy images were acquired to determine the intracellular uptake of BRNVs and DOX@BRNVs with or without 650 nm of laser (5 min, 90 mW/cm$^2$). A549 cells (1*10$^4$/well 24-well plate) were grown on cover slip in culture medium for 24 hr at 37° C. Cells were treated with culture medium, DOX (5 μg/ml), BRNVs (20 μg/ml), DOX@BRNVs (DOX; 5 μg/ml, BRNVs; 20 μg/ml) or DOX@BRNVs (DOX; 5 μg/ml, BRNVs; 20 μg/ml)+650 nm of light (5 min, 90 mW/cm$^2$) at 37° C. for 4 h. Cells were then fixed with 4% paraformaldehyde, stained with 4',6'-diamidino-2-phenylindole (DAPI; Sigma-Aldrich), mounted with fluorescence mounting medium (Dako, Carpinteria, CA), and visualized by confocal laser-scanning microscope (LSM 710; Carl Zeiss Microimaging, Jena, Germany; excitation wavelength: 480 nm, emission wavelength: 530-670 nm).

MTT Assay

An MTT [3-(4,5-dimethylthiazol-2-yl)-2,5-diphenyltetrazoliumbromide] reduction assay was used to demonstrate the cytoprotectant effects of BRNVs and the effects of light exposure (450 nm) on DOX@BRNVs's anticancer effects. CHO-K1 cells seeded at density of 7,000 cells per well in 96-well plates and were grown in culture medium for 24 hr at 37° C. After medium was removed, fresh medium, 500 μM of hydrogen peroxide, or various concentrations of BRNVs supplemented with or without 500 μM of hydrogen peroxide was treated into each well for 8 hr. A549 cells (0.7*10$^3$/well 96-well plate) were grown in culture medium for 24 hr at 37° C. After medium was removed, cells were incubated with fresh medium as a control, DOX (5 μg/ml), DOX@BRNVs (DOX; 5 μg/ml, BRNVs; 20 μg/ml), DOX@BRNVs (DOX; 5 μg/ml, BRNVs; 20 μg/ml)+650 nm of light (5 min, 90 mW/cm$^2$) or BRNVs (20 μg/ml) for 15 hr. After then, cells were washed with DPBS and further incubated with fresh medium for 20 hr. Next, after cells were washed, 100 μl of fresh culture medium was added to each well, followed by 20 μl of MTT solution (5 mg/mL in PBS) before 200 μl of DMSO to each well to dissolve the resulting formazan crystals. After pipetting each well for completely dissolving of the formazan crystal, the absorbance was measured at 540 nm using a 96-well plate reader.

Tube Formation Study Using HUVEC Cell Lines

A 50 μl of growth factor-reduced Matrigel (BD bioscience) was plated to 96-well plate at a horizontal level that allows the Matrigel to distribute evenly, and incubated for 30 min at 37° C. to form a gel that offers an environment for HUVECs to from capillary-like structures typically not observed on normal cell culture plates. HUVEC cells (7.5*10⁴/well) in EBM-2 culture medium supplemented with VEGF (20 ng/ml), BRNVs (2.5 μg/ml or 25 μg/ml), or VEGF (20 ng/ml)+BRNVs (2.5 μg/ml or 25 μg/ml) were loaded on the top of Matrigel. Following incubation at 37° C. overnight, cells were washed with DPBS and visualized under a fluorescence microscope.

Animal Housing

All animal experiments were carried out in female C57BL/6 mice (6 weeks, 17-20 g, Orient bio, seoul, korea), ICR mice (6 weeks, 20-25 g) or Balb/c nudemice (6 weeks, 20-25 g, Orient bio). Mice were housed under pathogen-free conditions (25° C.). Animal care was provided in accordance with the guidelines of the animal care facility at Korea advanced institute of Science and Technology. All surgery was performed under isoflurane.

PK Profile of BRNVs

ICR mice (6 weeks, 20-25 g) were injected intravenously via the tail vein with DOX (4 mg/ml), BRNVs (40 mg/kg) or DOX@BRNVs (DOX; 4 mg/kg, BRNVs; 40 mg/kg) and sacrificed at different times (0.0167, 0.5, 1, 4, 8, 12, 24 h) after injection. Blood (450 μL) was collected via orbital plexus and mixed with BD Microtainer® tubes (BD biosciences), after which the sample was immediately centrifuged at 13,000 rpm for 5 min. MeOH (100 μL) was added to the serum and centrifugation was performed at 12,000 rpm for 10 min. Free DOX in samples was determined by HPLC. BRNVs were determined by UV/Vis spectroscopy at 450 nm of wavelength.

Evaluation of Anti-Inflammation Effects

C57BL/6 Mice were housed in groups of 5 mice per cage and acclimatized for 1 week before entering the study. Mice received 3.5% (w/v) DSS (25,000 daltons; Tokyo Industry Chemicals, Tokyo) supplemented in the drinking water for 5 days followed by a regime of 10 days of water. Control healthy mice were allowed to drink only water. On day 1, 100 μl of BRNVs (125 mg/kg) or PBS was injected into mice via intravenous injection. On end day of experiment, mice were sacrificed and the entire colon was excised. Colon length was determined and washed with PBS.

A 1 cm of distal colons was fixed with 4% (v/v) buffered formalin and 70% (v/v) alcohol and embedded in paraffin. Then, tissue sections of the distal colon were prepared and stained with H&E. Histology of the colon was analysed using a microscope. Severity was scored as previously described [Garrett Ws et al (Cell 2010), Xiao-Dong Li et al (PNAS 2011)]. Briefly, colonic epithelial damage was assigned scores as follows: 0=normal; 1=hyperproliferation, irregular crypts, and goblet cell loss; 2=mild to moderate crypt loss (10-50%); 3=severe crypt loss (50-90%); 4=complete crypt loss, surface epithelium intact; 5=small- to medium-sized ulcer (<10 crypt widths); 6=large ulcer (≥0 crypt widths). Infiltration with inflammatory cells was assigned scores separately for mucosa (0=normal, 1=mild, 2=modest, 3=severe), submucosa (0=normal, 1=mild to modest, 2=severe), and muscle/serosa (0=normal, 1=moderate to severe). Scores for epithelial damage and inflammatory cell infiltration were added, resulting in a total scoring range of 0 to 12.

MPO Activity and Measurement of Inflammatory Cytokine

Using the remaining colon tissue samples, myeloperoxidase (MPO) activity and concentrations of TNF-alpha, IL-1-Beta, IL-6 and IFN-Gamma were determined. MPO activity was measured according to the previous method (Wilson et al. Nature materials 2010). Briefly, to check MPO activity, colon's segment was homogenized in 1:10 (w/v) 50 mM phosphate buffer (pH 6.0) containing 0.5% hexadecyltrimethyl ammonium bromide using homogenizer (polytron) at 4° C. After sonication for 10 sec, freeze-thaw three times, each sample was centrifuged at 14,000 rpm for 5 min. A 10 μl of supernatant was added to 290 μl of 50 mM phosphate buffer (pH 6.0) containing a 0.167 mg/ml of o-dianisidine hydrochloride and 0.0005% hydrogen peroxide, and the change in absorbance at 460 nm was measured for 5 min. One unit of MPO activity is defined as that degrading 1 μmol of peroxide per minute at 25° C. Concentrations of IL-1β, IL-6, IFN-γ and TNF-α were measured using an enzyme-linked immunosorbent assay kit for mice (R&D) according to the manufacturer's instructions.

Assessment of Inflammation Site Targeting Ability of BRNVs

DSS induced murine colitis model (C57BL/6 Mice) and control healthy mice were prepared as described in the previous section. ICG was loaded to BRNVs. Briefly, on day 5, a 100 μl of ICG@BRNVs (ICG; 17 μg, BRNVs; 340 μg) was injected into mice via intravenous injection. After 6 hrs, mice were sacrificed and the major organs (colon, kidney, liver, spleen, lung, heart) were collected. Fluorescence intensities from major organs in each group were visualized by in vivo imaging system using an exposure time of 5 s and via the ICG filter channel.

Anticancer Ability of BRNVs

Tumor xenograft mouse model was prepared through A549 tumor cell line S.C injection (1*10⁶) into dorsal flanks of six-week-old female BALB/c nude mice until tumor volume was at least 80-120 mm³ using Balb/c Nude mice. Tumor bearing mice were randomly divided into groups of four (day 0), minimizing weight and tumor size differences, and then given DOX (2 mg/kg), BRNVs (20 mg/kg), DOX@BRNVs (DOX; 2 mg/kg, BRNVs; 20 mg/kg), DOX@BRNVs (DOX; 2 mg/kg, BRNVs; 20 mg/kg)+650 nm of light (30 min after injection for 5 min, 200 mW/cm²), DPBS as a control by means of a I.V. injection five times at predetermined day (day 0, 3, 6, 9, 12). At each day, tumor volume in each group was measured using vernier calipers. Tumor volume was calculated using the formula, (length×width×height)/2.

Toxicity Evaluation of BRNVs

Toxicity experiments were carried out with healthy mice or DSS-induced colitis mice (6 weeks, C57/BL6 female mice). Mice were injected through tail vein with BRNVs (150 mg/ml) or an equal volume of PBS. Over a one-week period, mice were observed for behavioural changes and weight was monitored. Mice were then killed and then major organs (liver, lung, kidney, spleen) were collected for analyzing organ toxicity.

EPR Effect Evaluation

For this evaluation, nude mice bearing tumor model were prepared through A549 tumor cell line S.C injection (1*10⁶) into dorsal flanks of six-week-old female BALB/c nude mice. After 3 weeks, BRNVs (25 mg/kg) or PBS (100 μl) as a control was treated through IV injection via tail vein of nude mice. After 24 hr, each group of nude mice was sacrificed and then major organs (Liver, Heart, Spleen, Kidney and Lung) and tumor were collected, and an optical image of major organs and tumor in each group was acquired by in vivo imaging system (IVIS) Optical images were acquired using an exposure time of 5 sec and via the GFP filter channel.

Results

Synthesis of PEGylated Bilirubin

For the conjugation of Bilirubin's one of two carboxylic groups with mPEG2000-NH₂, methoxy polyethlyleneglycol 2000 having terminal amine group was used. (Scheme I)

Figure 2:
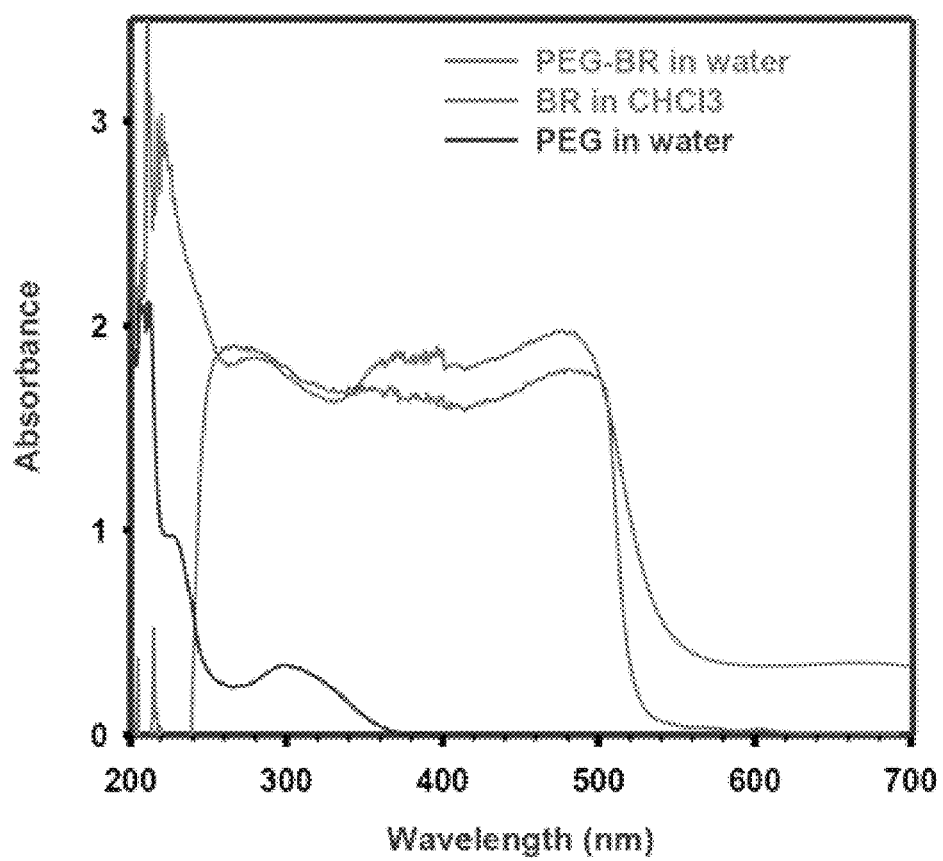
FIG. 2 shows UV spectrum results of PEG-BR.
Figure 3:
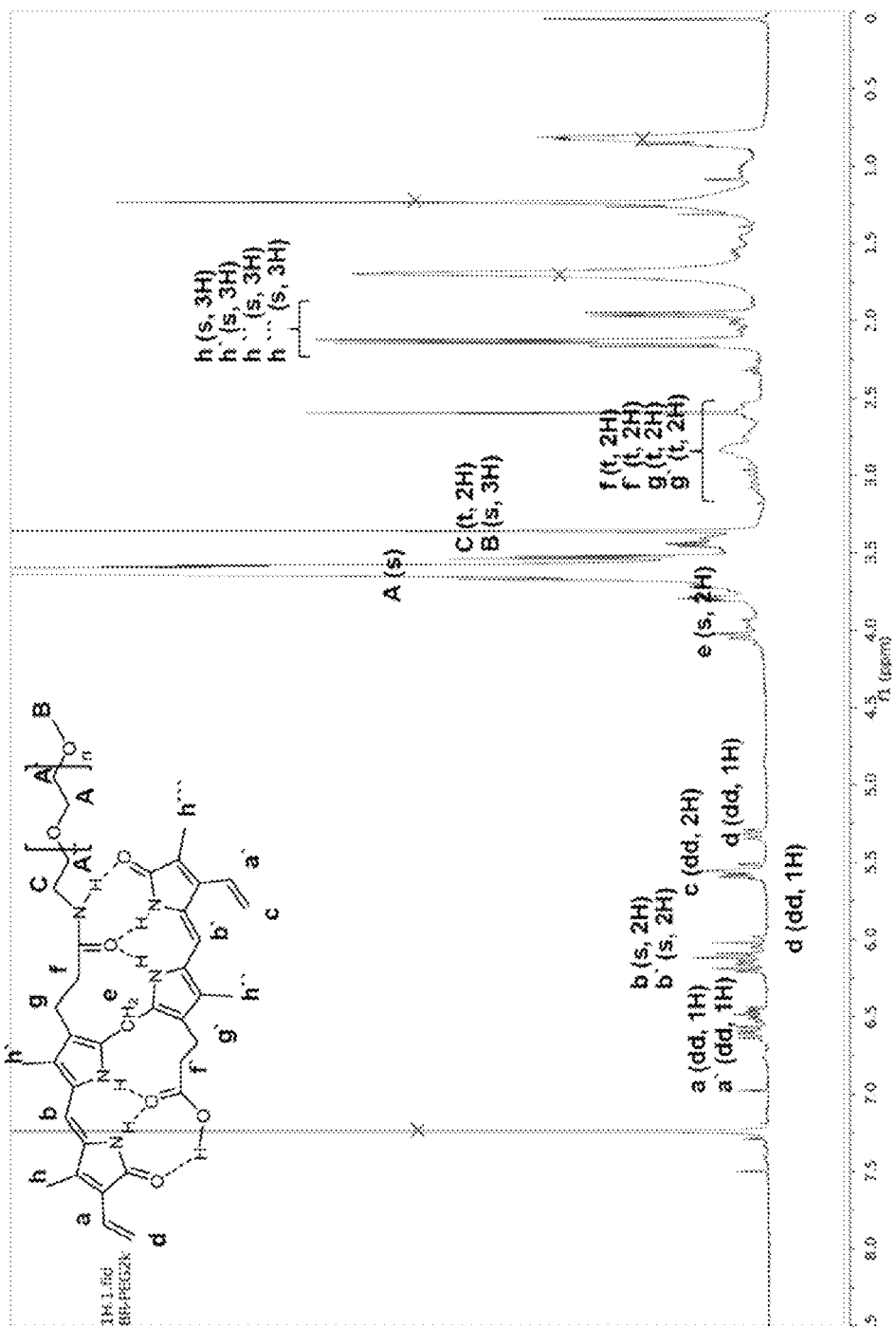
FIG. 3 shows $^1$H-NMR results of PEG-BR.

After activation of bilirubin with EDC in chloroform, a TEA and mPEG2000-NH$_2$ was added to this solution to yield PEG-BR and then, we acquired PEG-BR through purification process. It was confirmed that PEG-BR was synthesized correctly through MALDI-TOF (FIG. 1), UV spectra (FIG. 2) and $^1$H-NMR (FIG. 3).

BRNVs Preparation

Figure 4:
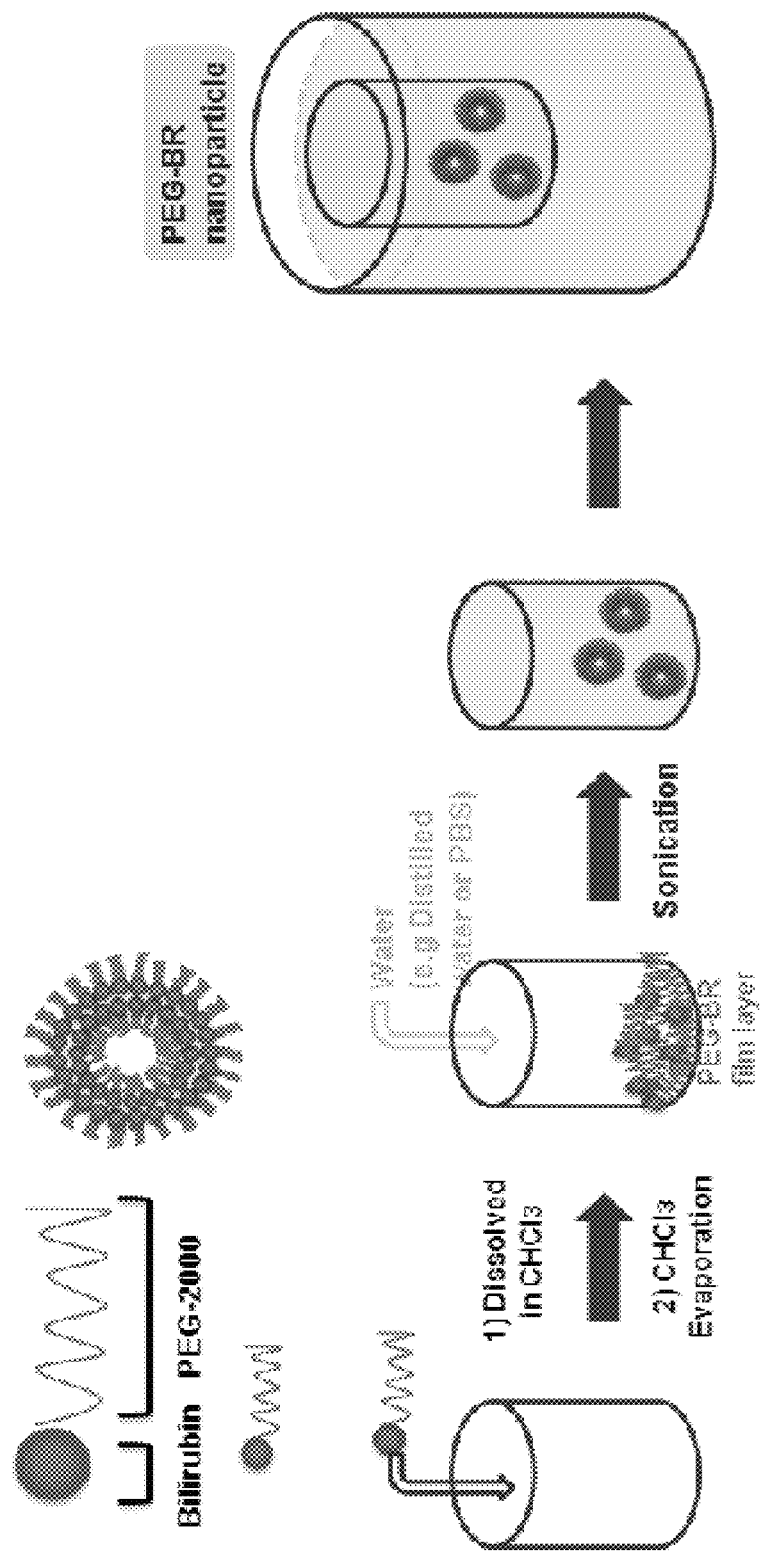
FIG. 4 shows a synthetic procedure of bilirubin nanoparticles (BRNVs) according to the present invention.

BRNVs were prepared using film layer method using acquired PEG-BR conjugate. PEG-BR was dissolved in the chloroform and then dried under a stream of nitrogen gas and further dried under vacuum to make the film layer, some Phosphate buffer was added to the film layer and then sonicated for 10 min. Finally, BRNVs was acquired (FIG. 4).

Figure 5:
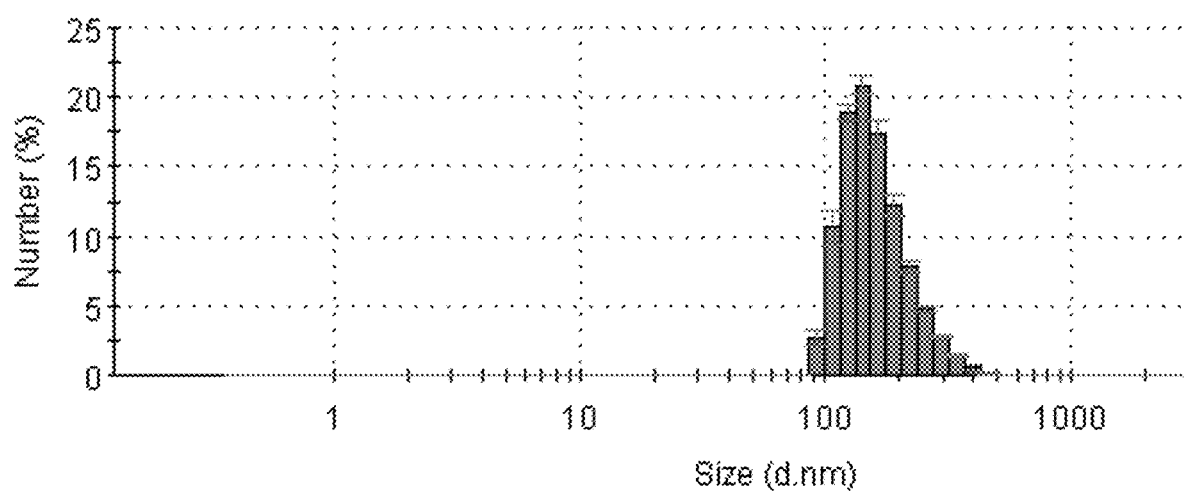
FIG. 5 shows the size of bilirubin nanoparticles according to the present invention.
Figure 6:
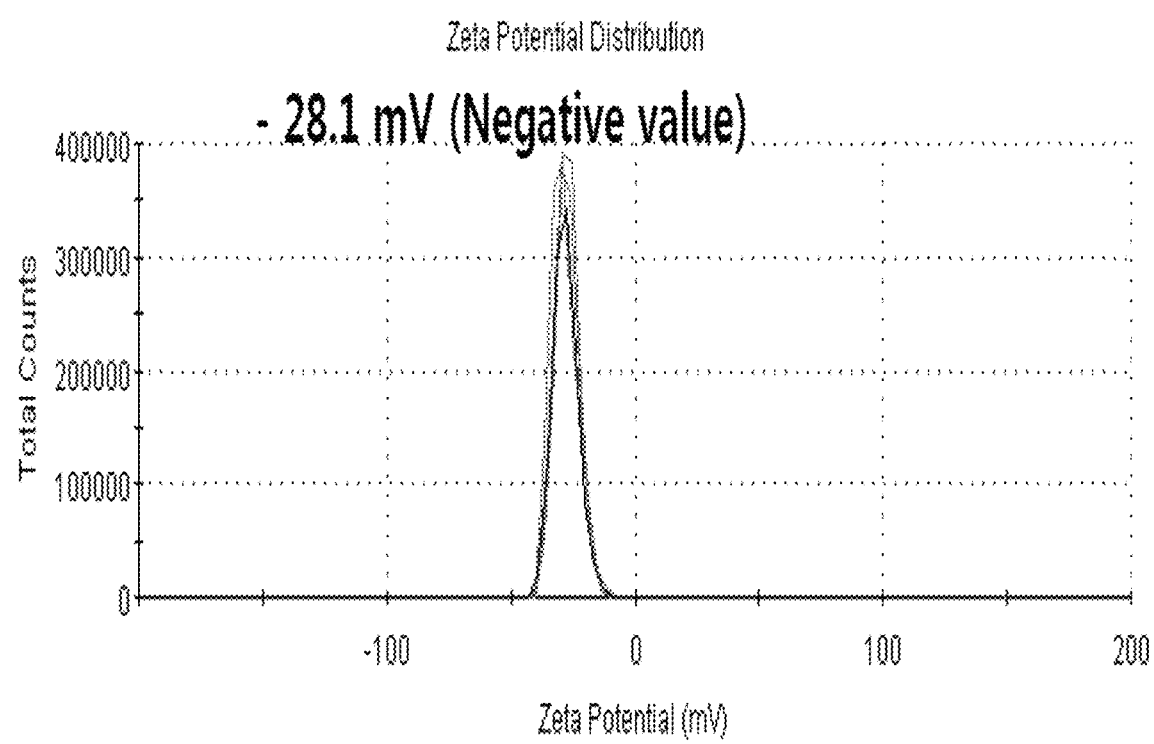
FIG. 6 shows the zeta potential of bilirubin nanoparticles according to the present invention.
Figure 7:
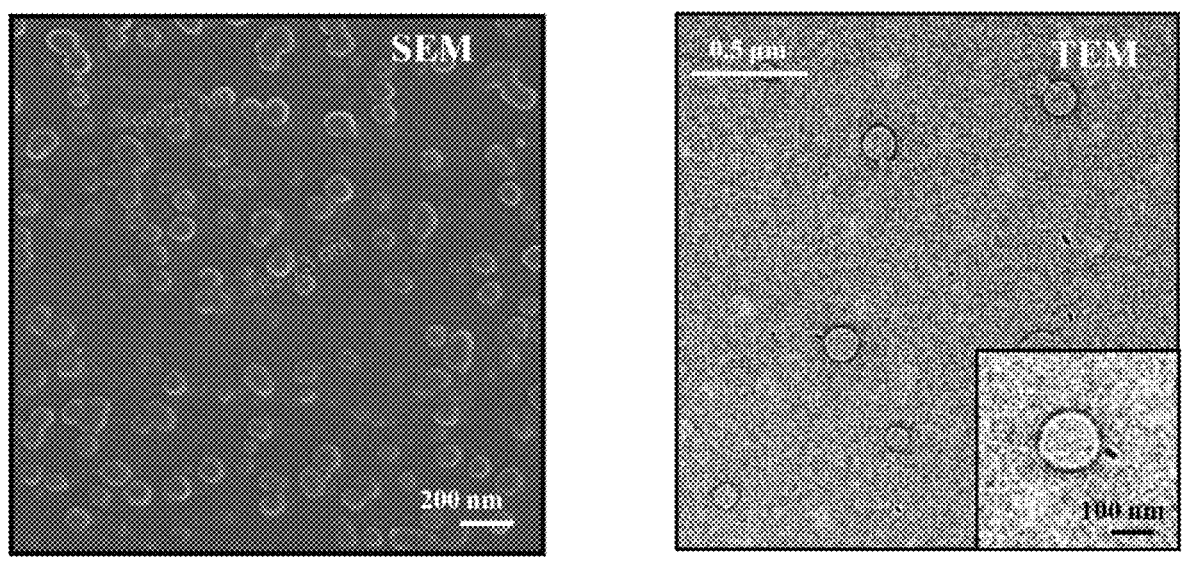
FIG. 7 shows SEM and TEM images of bilirubin nanoparticles according to the present invention.

To confirm the nanoparticle formation of PEG-BR, size and zetapotential, and SEM and TEM of BRNVs in PBS were acquired. It had an approximately 300 nm (FIG. 5) and –30 my (FIG. 6), respectively. BRNV's image was shown in FIG. 7. These results prove that amphipathic nature of the PEG-BR allows for the formation of the nanoparticle.

Critical Micelle Concentration of BRNVs

Figure 8:
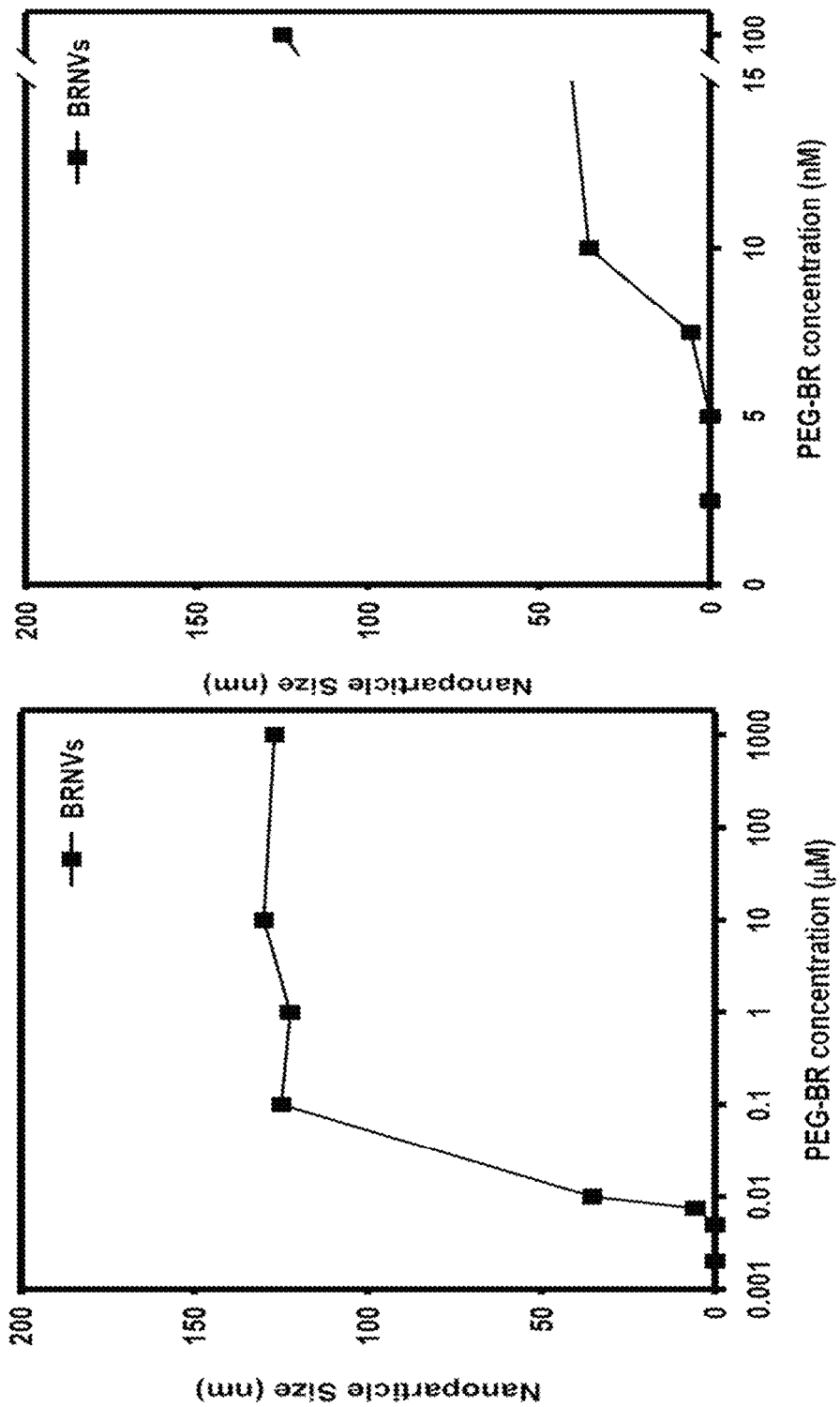
FIG. 8 shows the critical micelle concentration of bilirubin nanoparticles according to the present invention.

We checked the BRNV's critical micelle concentration. As shown in FIG. 8, nanoparticle was formed 100 nM (0.5 µg/ml) or more of PEG-BR.

BRNVs Stability

Figure 9:
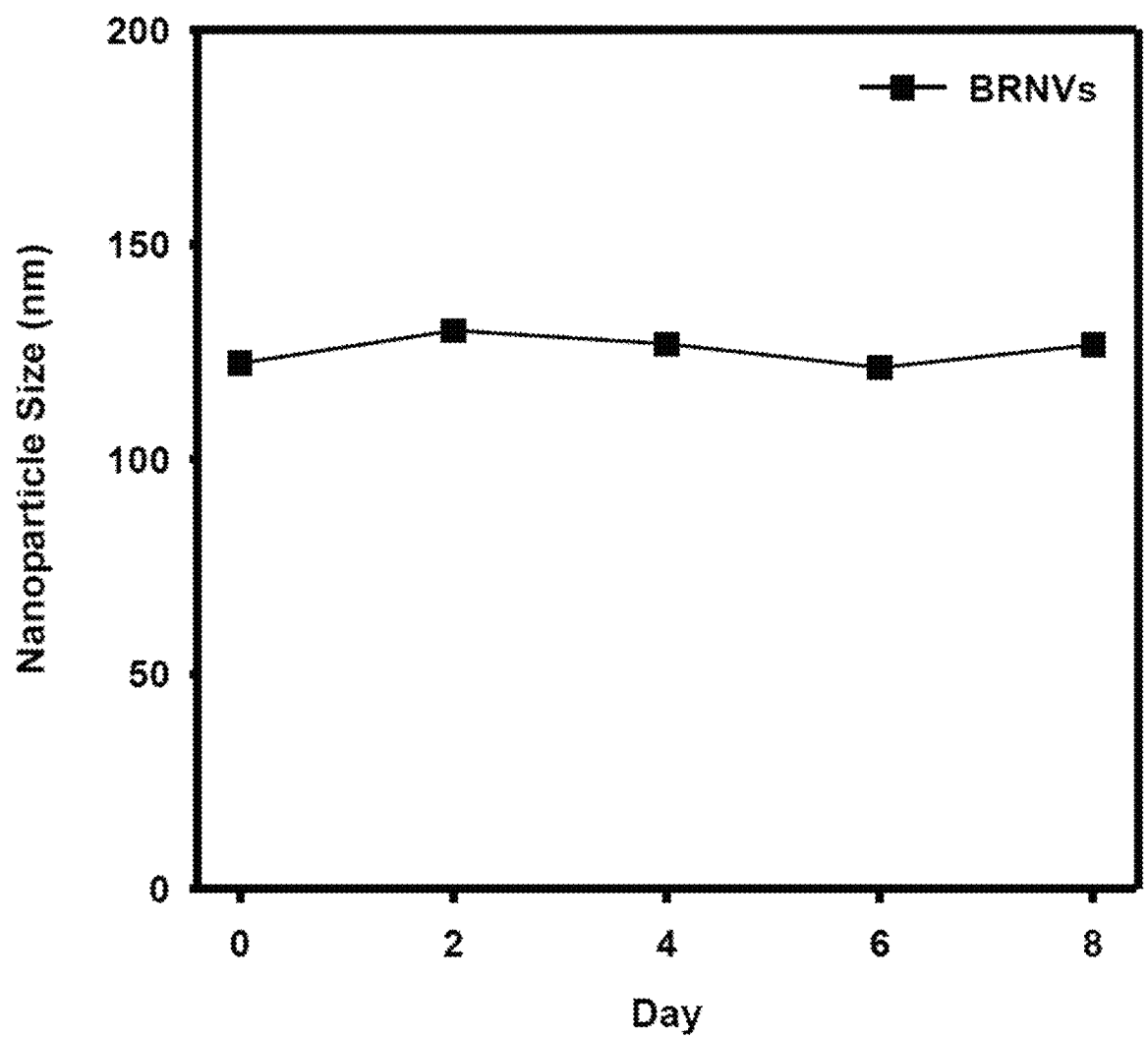
FIG. 9 shows stability of bilirubin nanoparticles according to the present invention.

To demonstrate the stability of BRNVs in PBS during storage at R.T, BRNV's size was monitored for 8 days. It was shown that nanoparticle's aggregation tendency was extremely low and their size's change didn't occurred (FIG. 9), indicating that nanoparticles are very stable during a storage.

Hydrogen Peroxide Scavenging of BRNVs (Antioxidant Effect)

Figure 10:
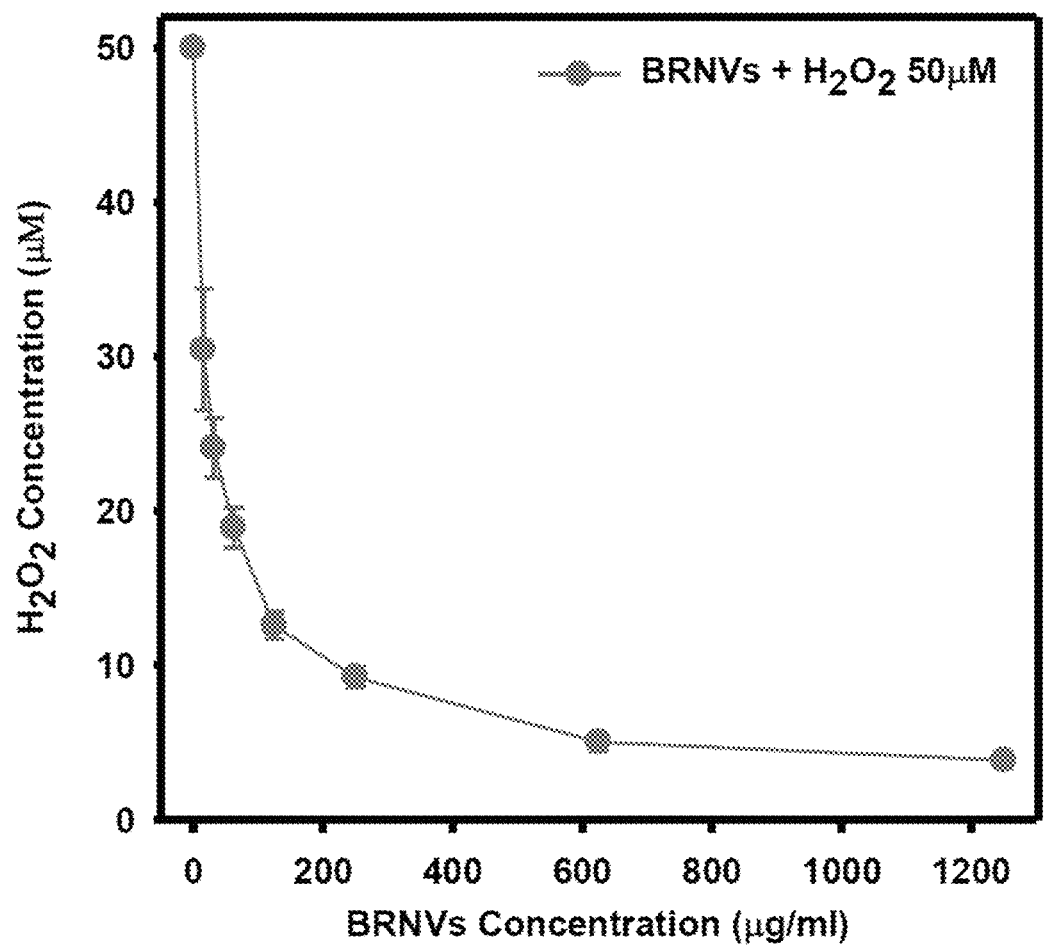
FIG. 10 shows an antioxidative activity of bilirubin nanoparticles according to the present invention.

To investigate an antioxidant effect of PEG-BR, hydrogen peroxide was treated with various concentrations of bilirubin nanoparticles, and then incubated for 40 min and then remaining concentration of the hydrogen peroxide was determined using HRP/dye systems by fluorescence intensity. As shown in FIG. 10, low levels of PEG-BR can scavenge large concentrations of hydrogen peroxide, indicating that BRNVs has powerful antioxidant effects.

ROS and Light-Responsive Disruption of BRNVs

Figure 11:
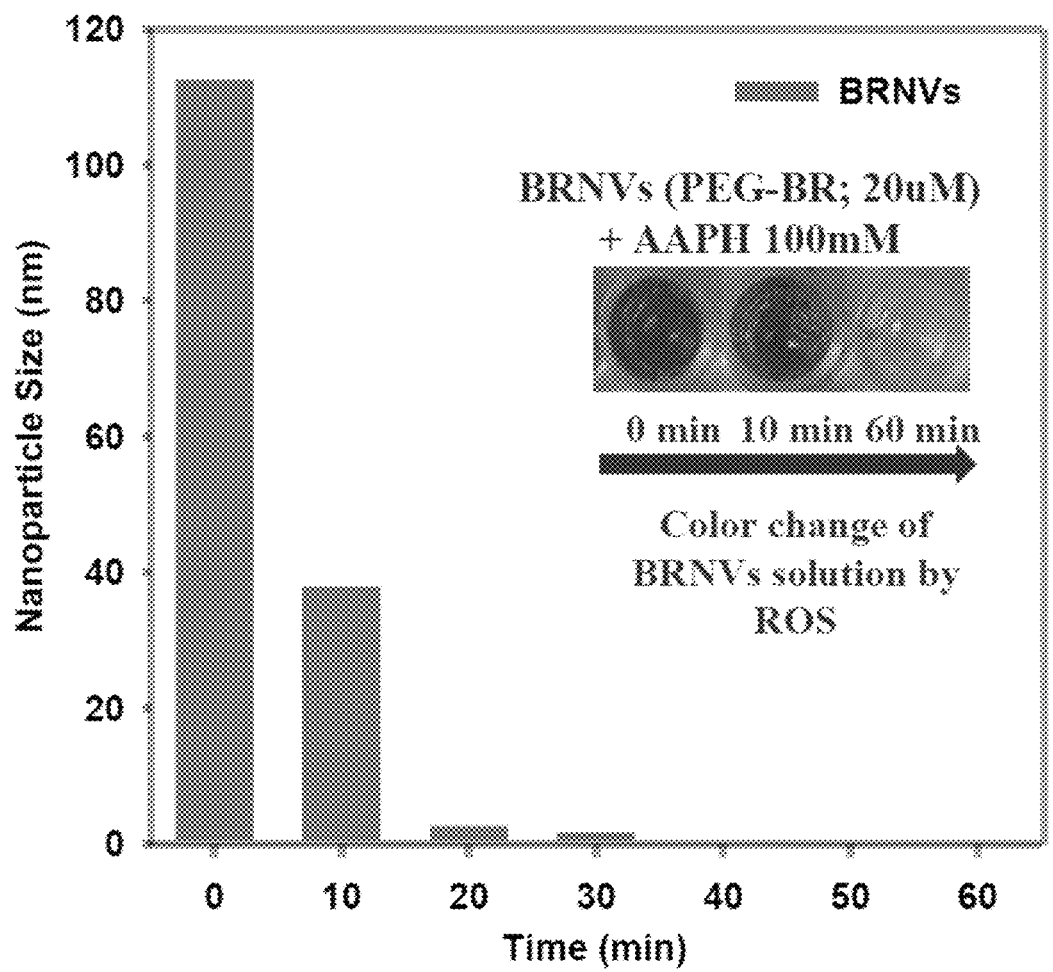
FIG. 11 shows the ROS-reactive disruption of bilirubin nanoparticles according to the present invention.
Figure 12:
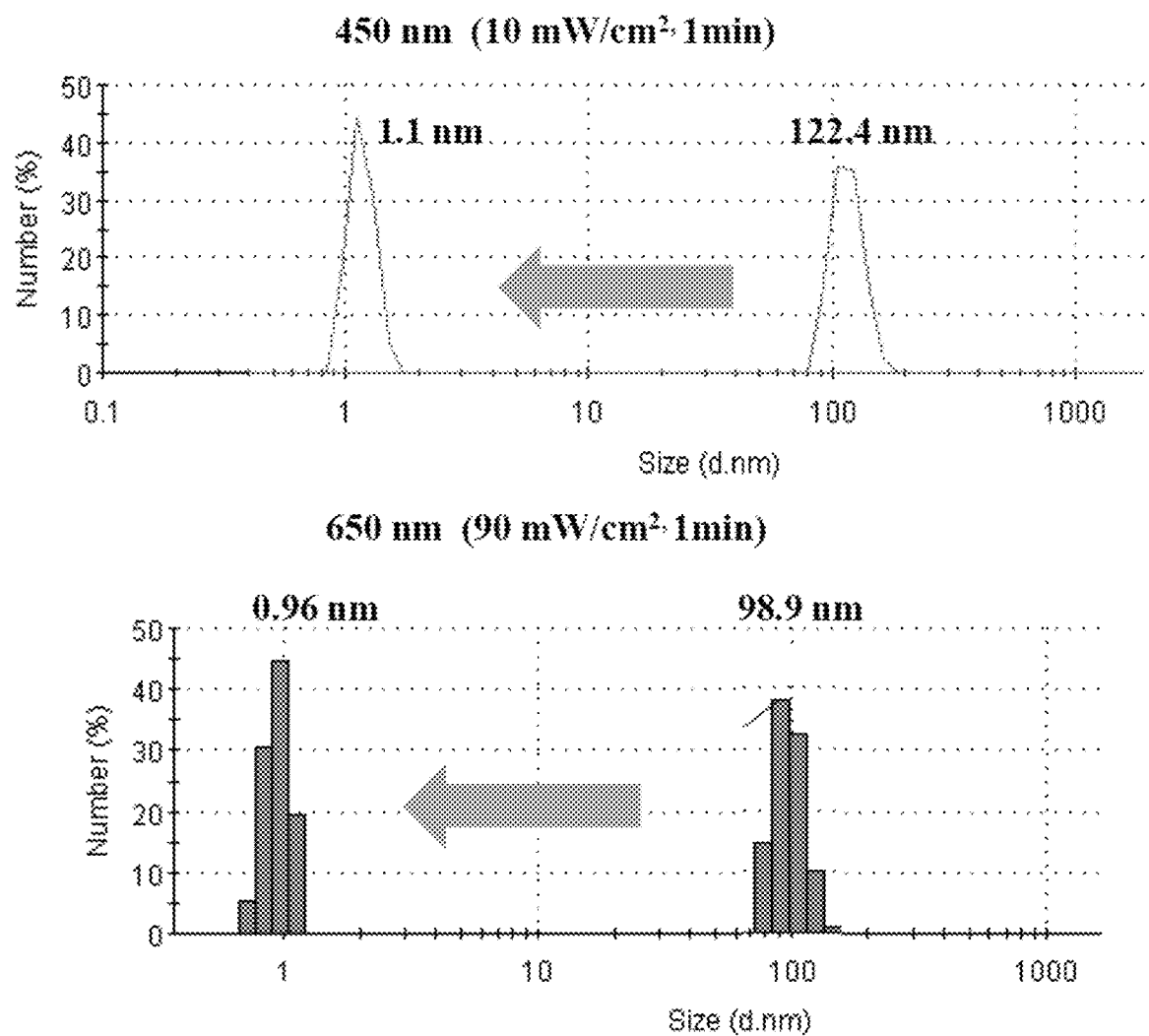
FIG. 12 shows the light-reactive disruption of bilirubin nanoparticles according to the present invention.

As shown in FIGS. 11 and 12, it was observed that the nanoparticles were disrupted within 1 min, which corresponds to a very quick time, under ROS and the irradiation of 650 nm and 450 nm laser.

Drug Encapsulation Ability

Figure 13:
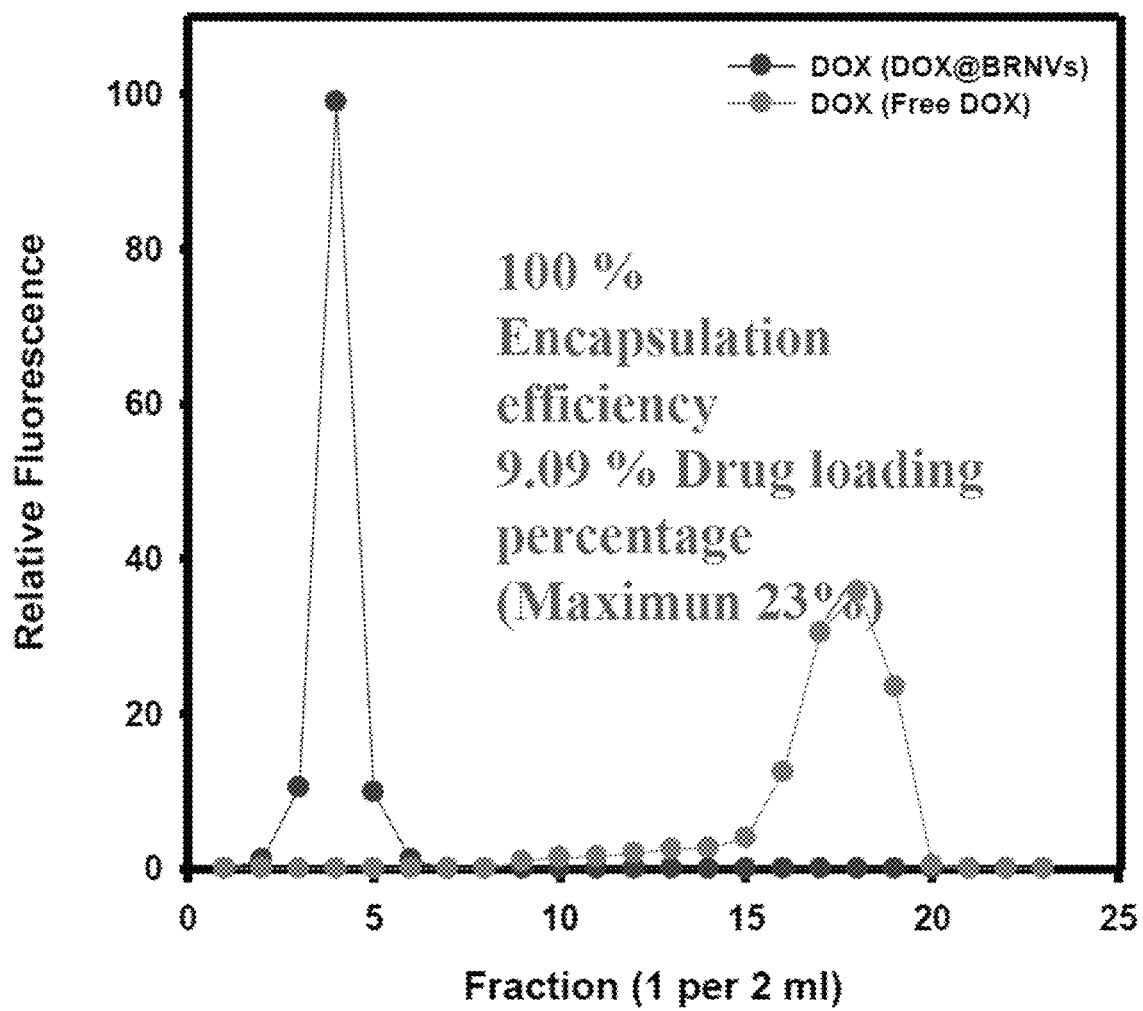
FIG. 13 shows hydrophilic drug encapsulation efficiency and drug loading efficiency of bilirubin nanoparticles according to the present invention.

Before assessing the ability of BRNVs to release encapsulated drug by light stimulus, hydrophilic drug and hydrophobic drug encapsulation capability of PEG-BR was investigated. For hydrophilic drug loading, hydrophilic drug was dissolved in water firstly, and then this solution was put into vial containing PEG-BR film layer. After nanoparticle formation, free hydrophilic drugs and PEG were eliminated by column separation. As a result, encapsulation efficiency and drug loading efficiency were 100% and 9.09%, respectively (FIG. 13).

Figure 14:
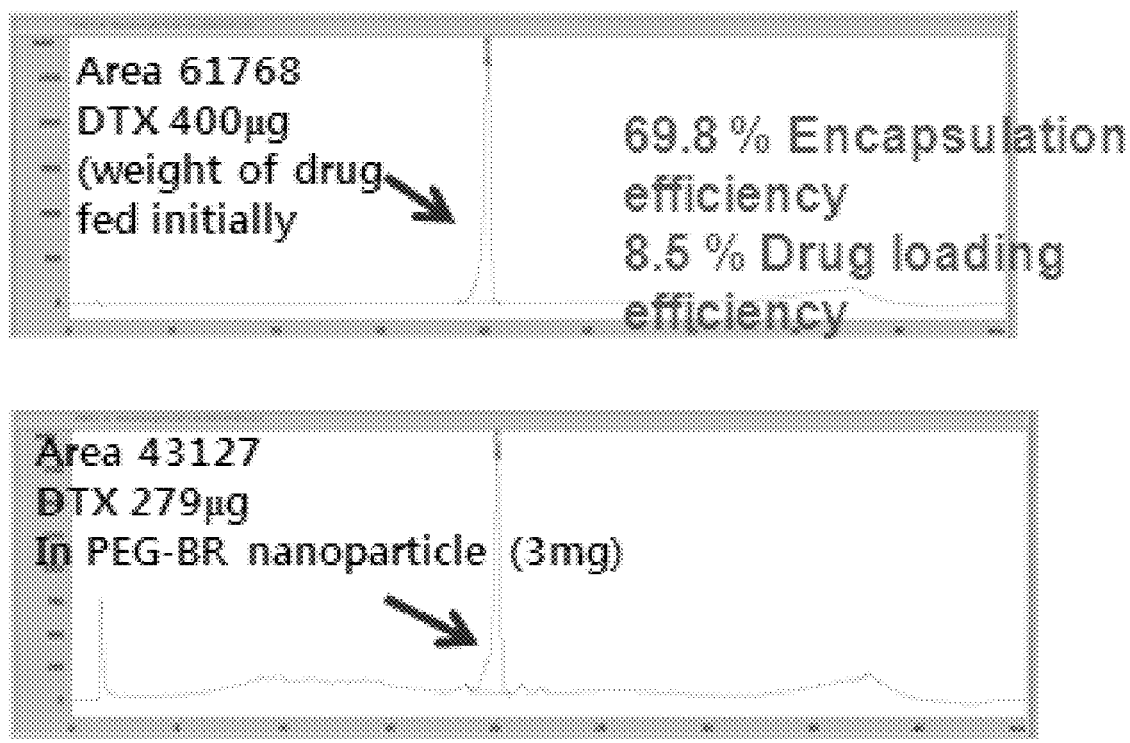
FIG. 14 shows hydrophobic drug encapsulation efficiency and drug loading efficiency of bilirubin nanoparticles according to the present invention.

For hydrophobic drug loading, hydrophobic drugs and PEG-BR were dissolved in chloroform, and then chloroform was evaporated to acquire film layer composing of PEG-BR and hydrophobic drug, and finally, water was poured into this film layer which results in some of hydrophobic drug encapsulation into nanoparticles. Nonencapsulated drug was eliminated by precipitation method. As a result, encapsulation efficiency and loading efficiency was 69.8% and 8.5%, respectively (FIG. 14).

Drug Release by Light

Figure 15:
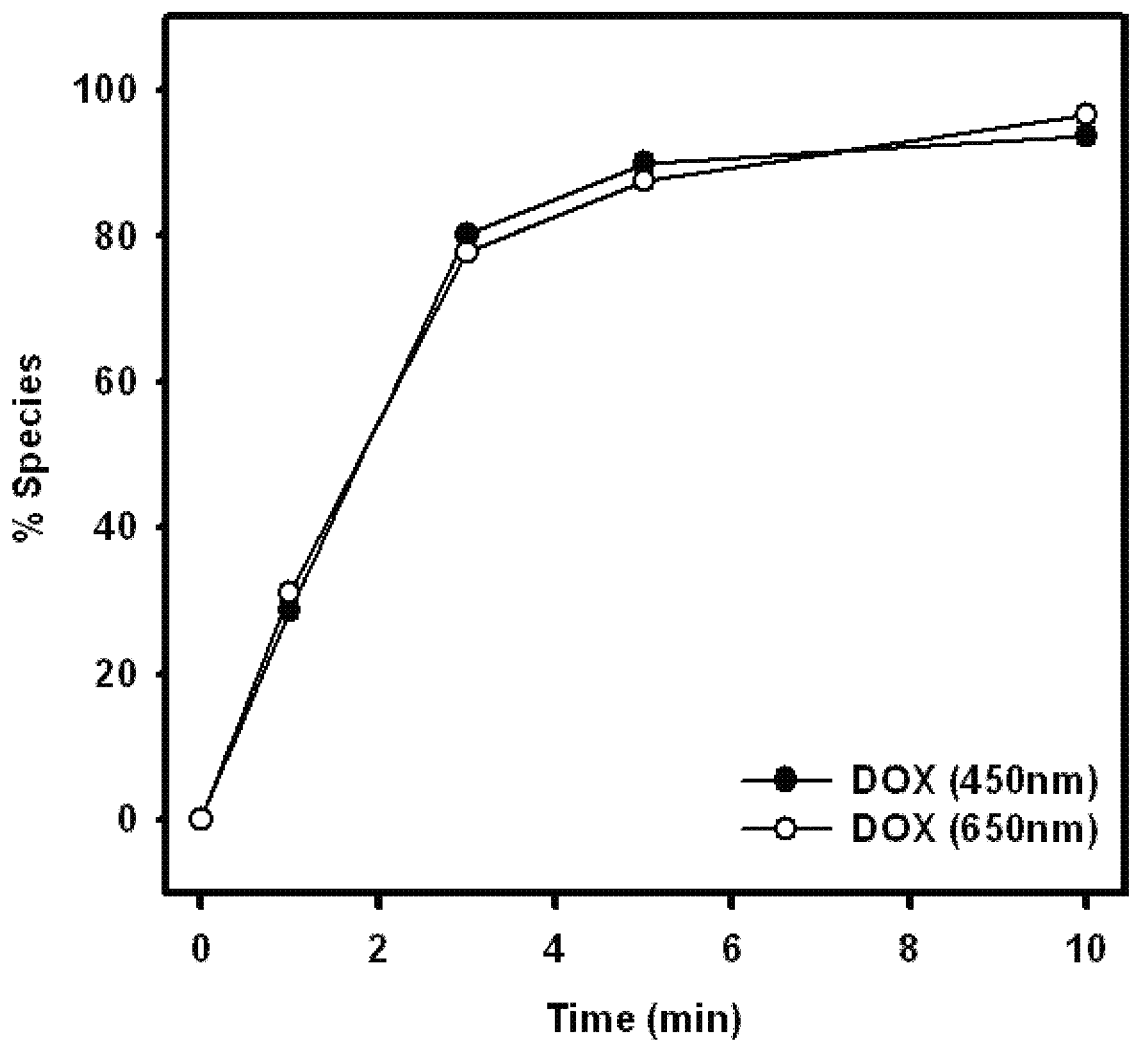
FIG. 15 shows the release of drug (doxorubicin) of bilirubin nanoparticles by the irradiation of light.
Figure 16:
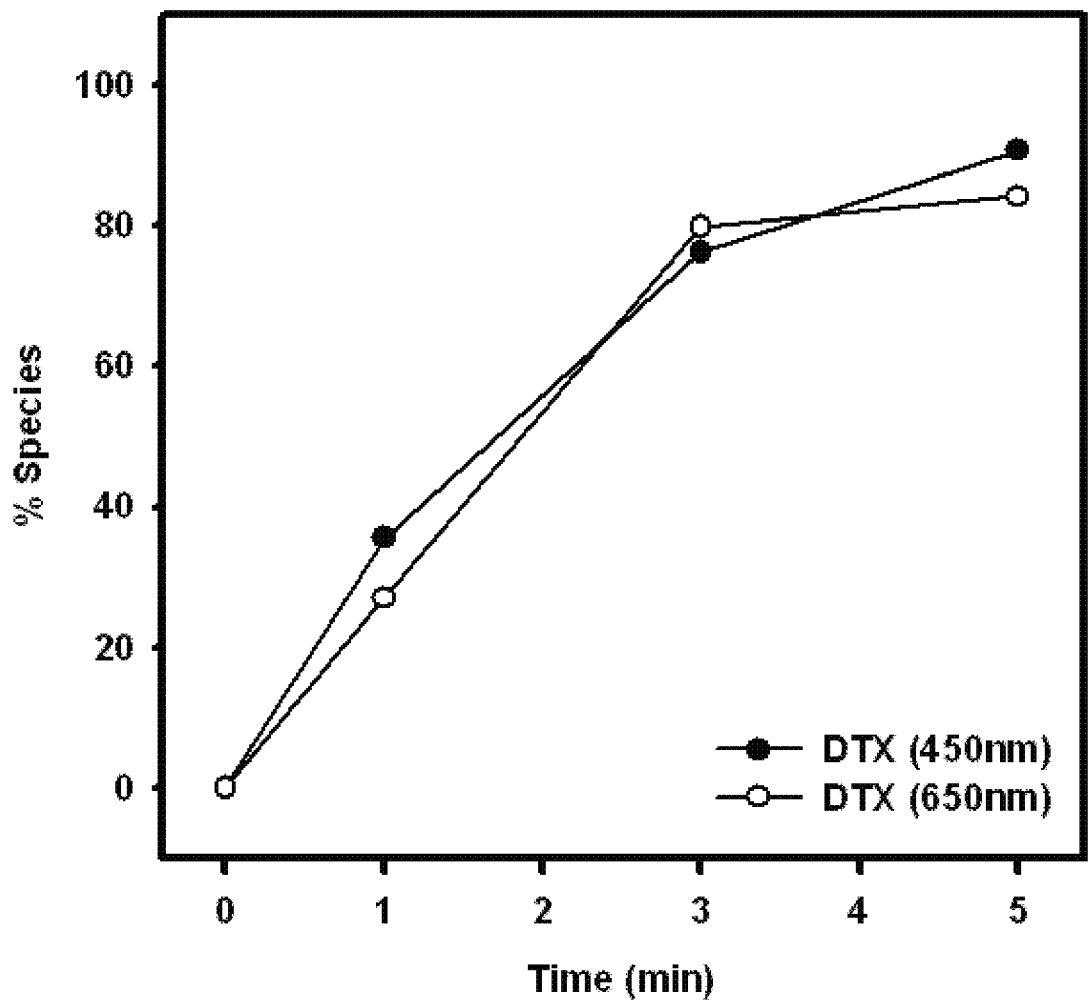
FIG. 16 shows the release of drug (docetaxel) of bilirubin nanoparticles by the irradiation of light.
Figure 17A:
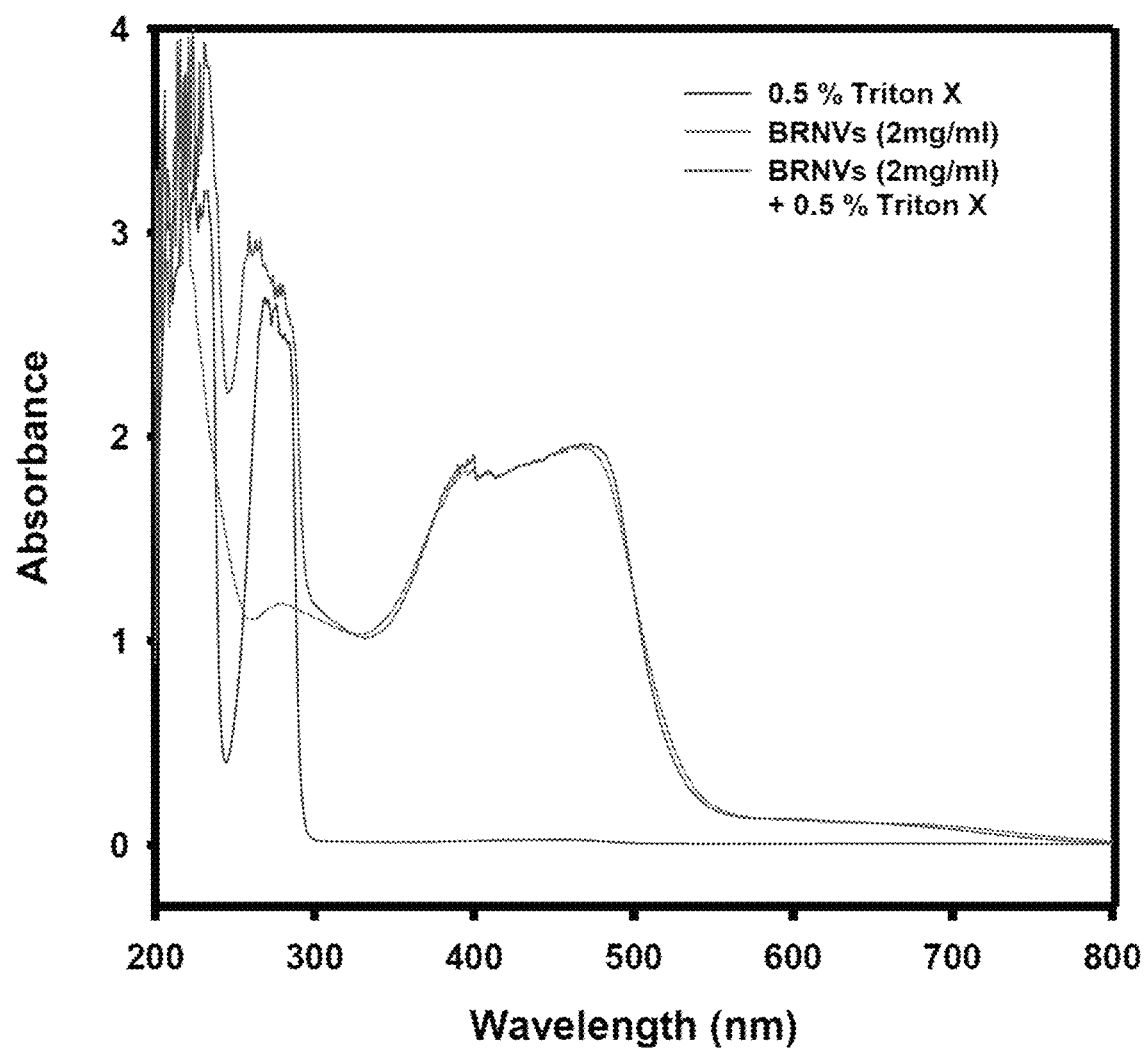
FIGS. 17a, 17b, 17c and FIG. 17d show fluorescent characteristics at the time of formation and disruption of bilirubin nanoparticles according to the present invention.
Figure 17B:
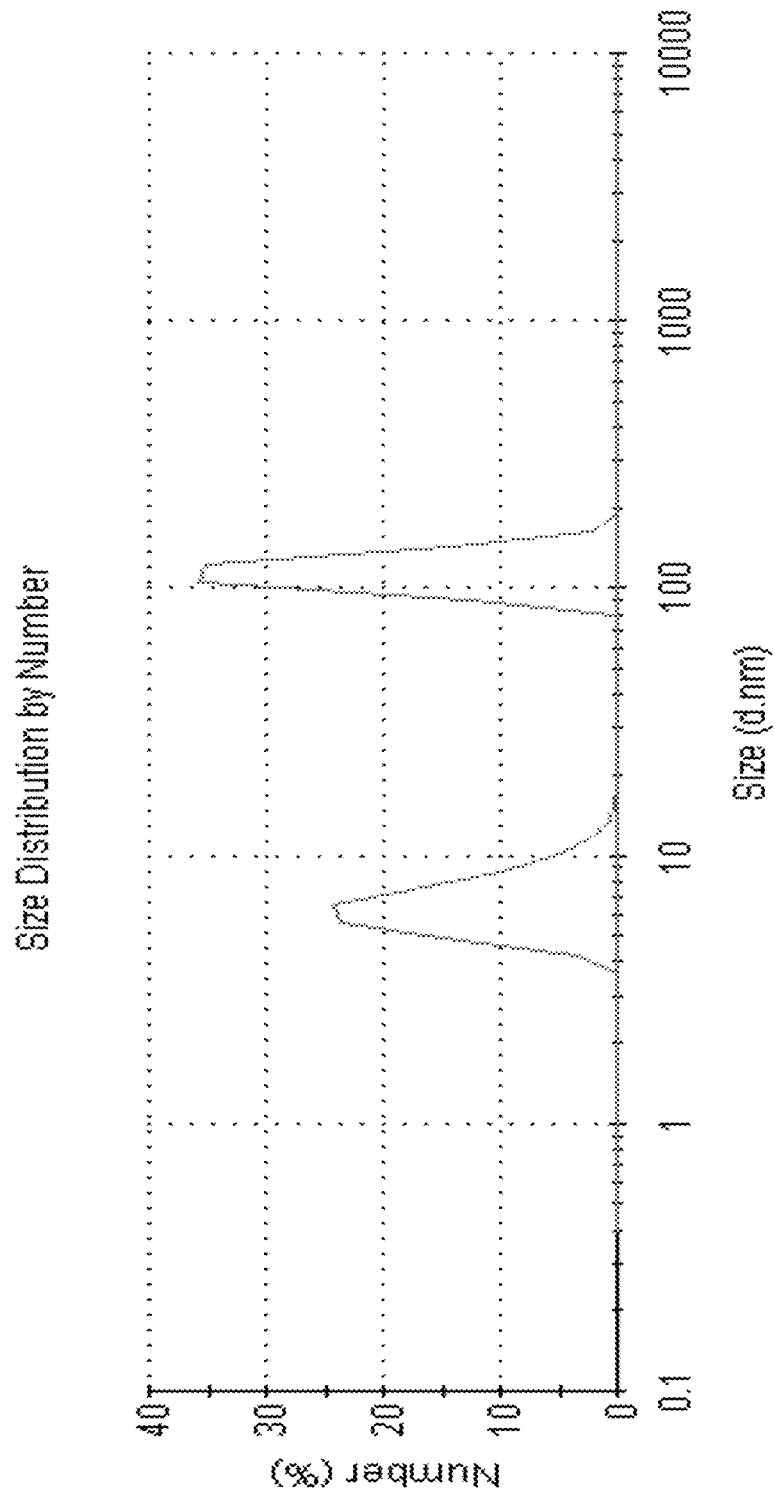
Figure 17C:
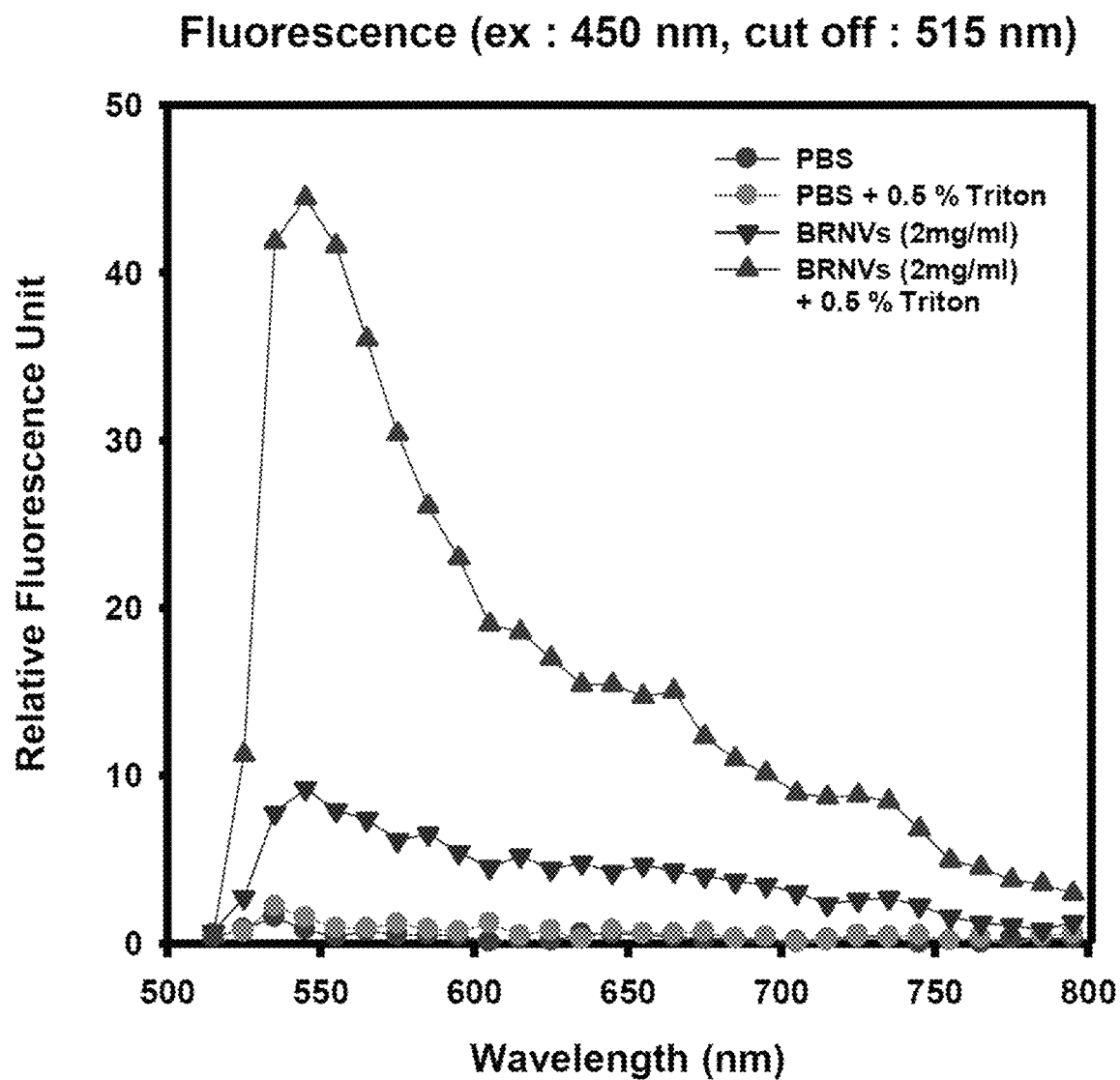
Figure 17D:
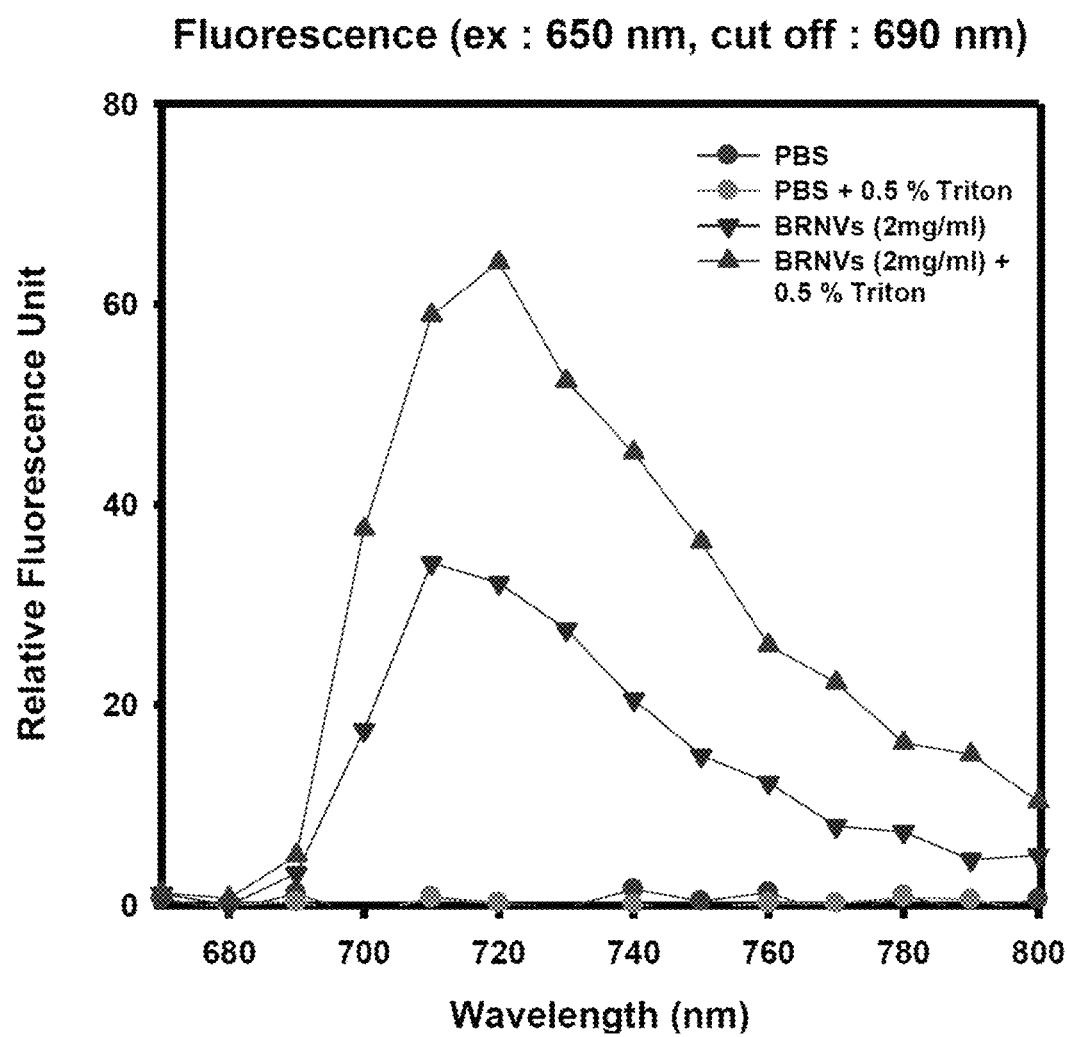

To investigate the nanoparticle's light sensitive disassembling ability, percentage of drug released from BRNVs was measured using extraction method during 450 nm laser irradiation. After laser irradiation, it was shown that drug was appeared in 1 minute and approximately 100% of drug was released in only 5 minutes (FIGS. 15 and 16). In addition, we hypothesized that BRNVs can be dissoluted by not only 450 nm (blue light) but also 650 nm (red light), and therefore to test this hypothesis, percentage of drug released from BRNVs was measured using extraction method during 650 nm laser irradiation. As a result, after laser irradiation, it was shown that drug was appeared in 1 minute and approximately 100% of drug was released in only 5 minutes (FIGS. 15 and 16). These results prove that BRNVs can be disassembled by both blue light and red light, and can release encapsulated drug.

BRNVs's Fluorescence Measurement

BRNVs's fluorescence was measured. If nanoparticles were formed, the fluorescence of the bilirubin layer of BRNVs would be self-quenched. As a result of measurement, as shown in FIGS. 17a to 17d, there was fluorescence at excitation wavelengths of 450 nm and 650 nm when the nanoparticles were formed and when the nanoparticles were disrupted, respectively.

ROS Generation Ability of BRNVs by Light

Figure 18:
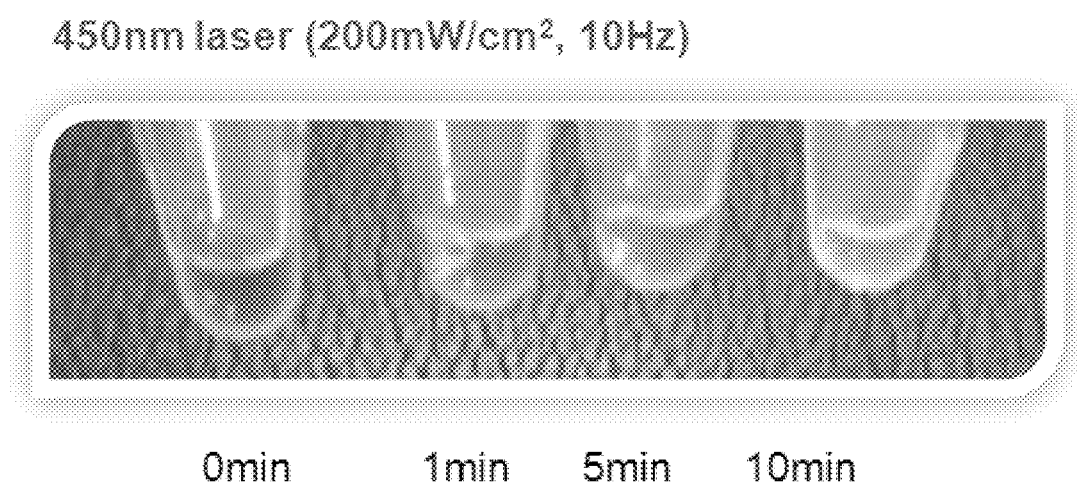
FIG. 18 shows ROS generating capacity of bilirubin nanoparticles by the irradiation of light (450 nm).

For checking whether nanoparticles can generate reactive oxygen species (ROS) by blue light, ROS generation ability was assessed. As shown in FIG. 18, BRNV's color became transparent during laser irradiation, indicating that BRNV's bilirubin core was converted into colorless oxidized products by ROS which generated from oxygen by bilirubin's photosensitizing effect during laser irradiation. These results indirectly tell us that BRNVs can generate ROS during laser irradiation.

Intracellular Uptake of BRNVs (Confocal Microscopy)

Figure 19:
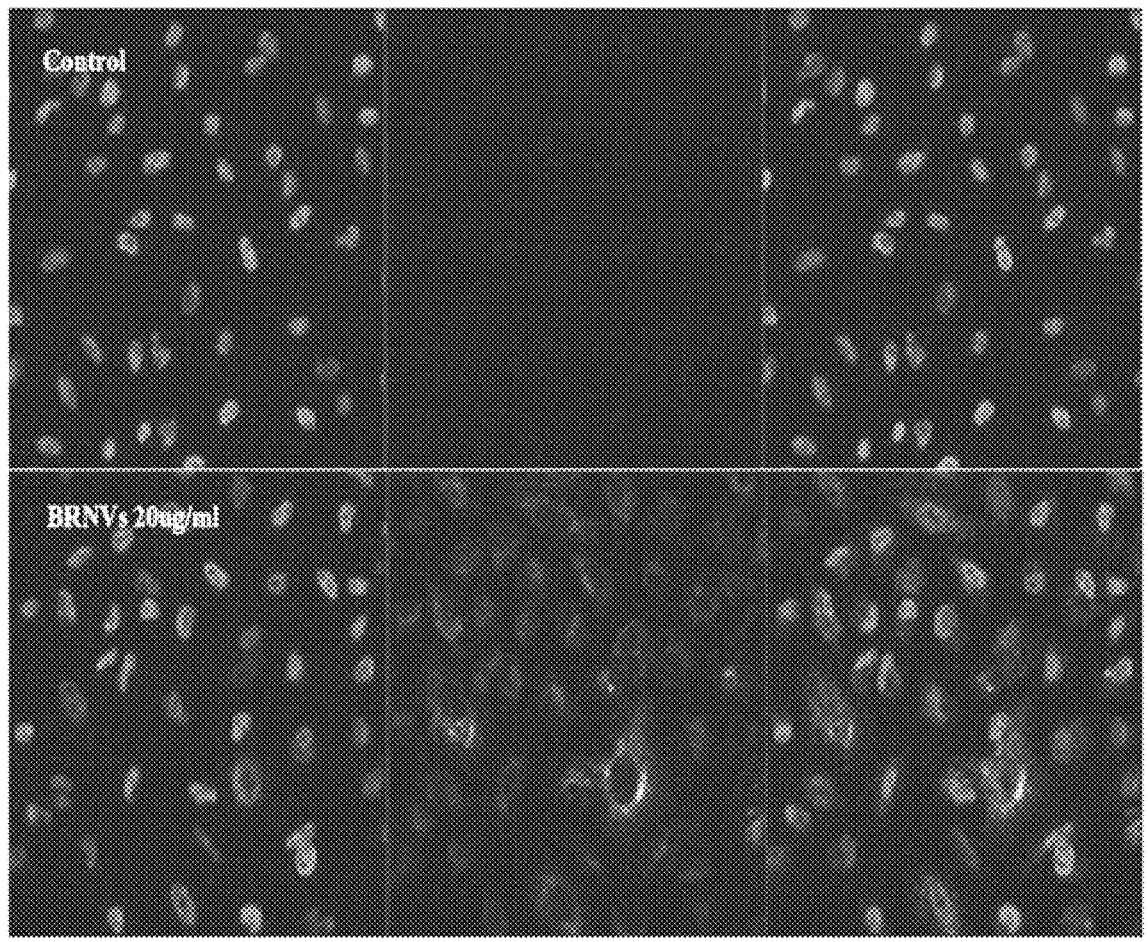
FIG. 19 shows the intracellular uptake of bilirubin nanoparticles according to the present invention.
Figure 20:
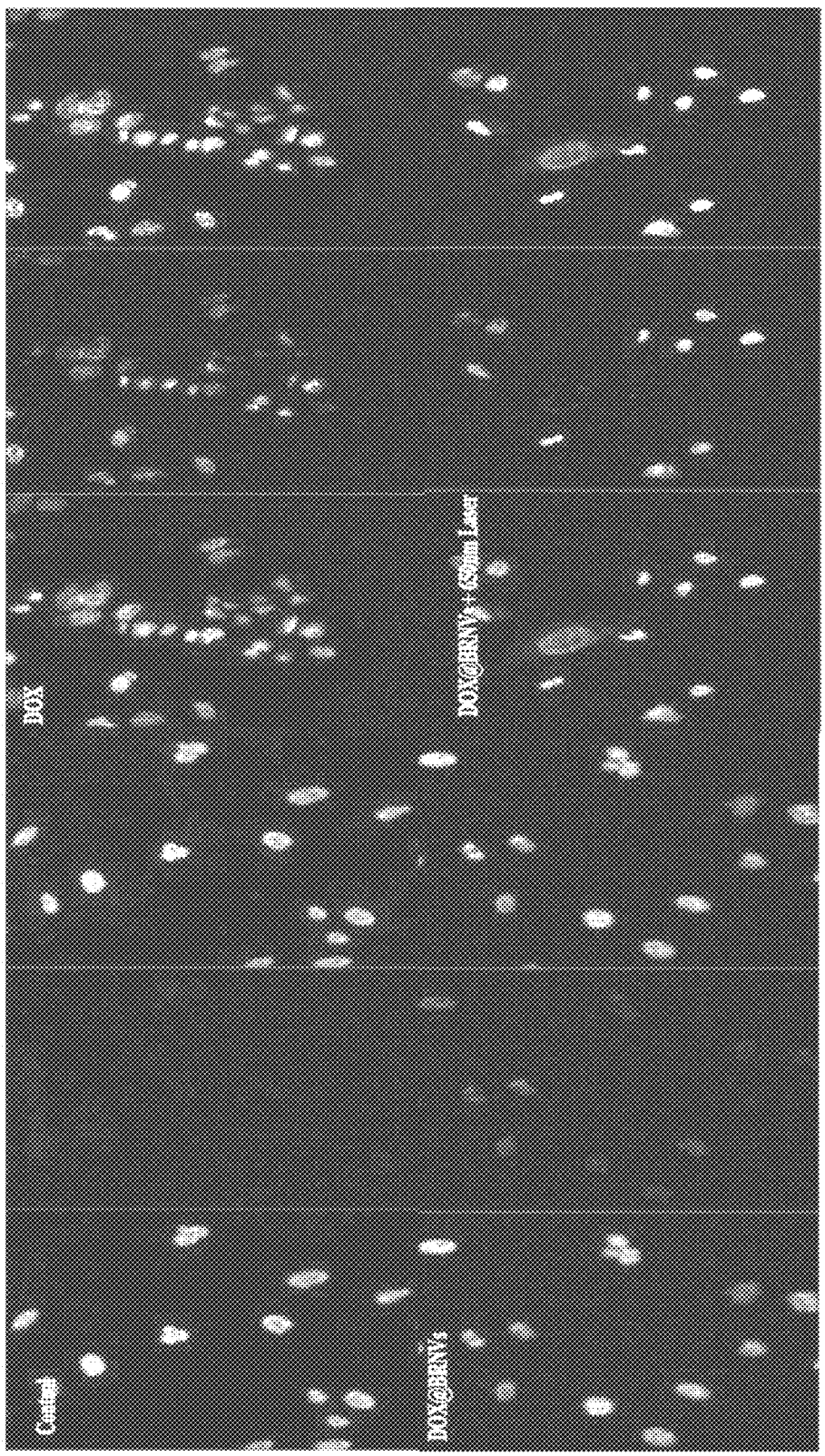
FIG. 20 shows the intracellular uptake, at the time of laser irradiation, of the doxorubicin-loaded bilirubin nanoparticles according to the present invention.

As shown in FIG. 19, the intracellular uptake of BRNVs occurred, and as shown in FIG. 20, doxorubicin was effectively released at the time of laser irradiation, and thus, DOX@BRNVs were shown to deliver doxorubicin into the cell nucleus as much as free doxorubicin entered the cell nucleus. This tendency was shown to decrease when DOX@BRNVs were not irradiated by laser.

MTT Assay Results

Figure 21:
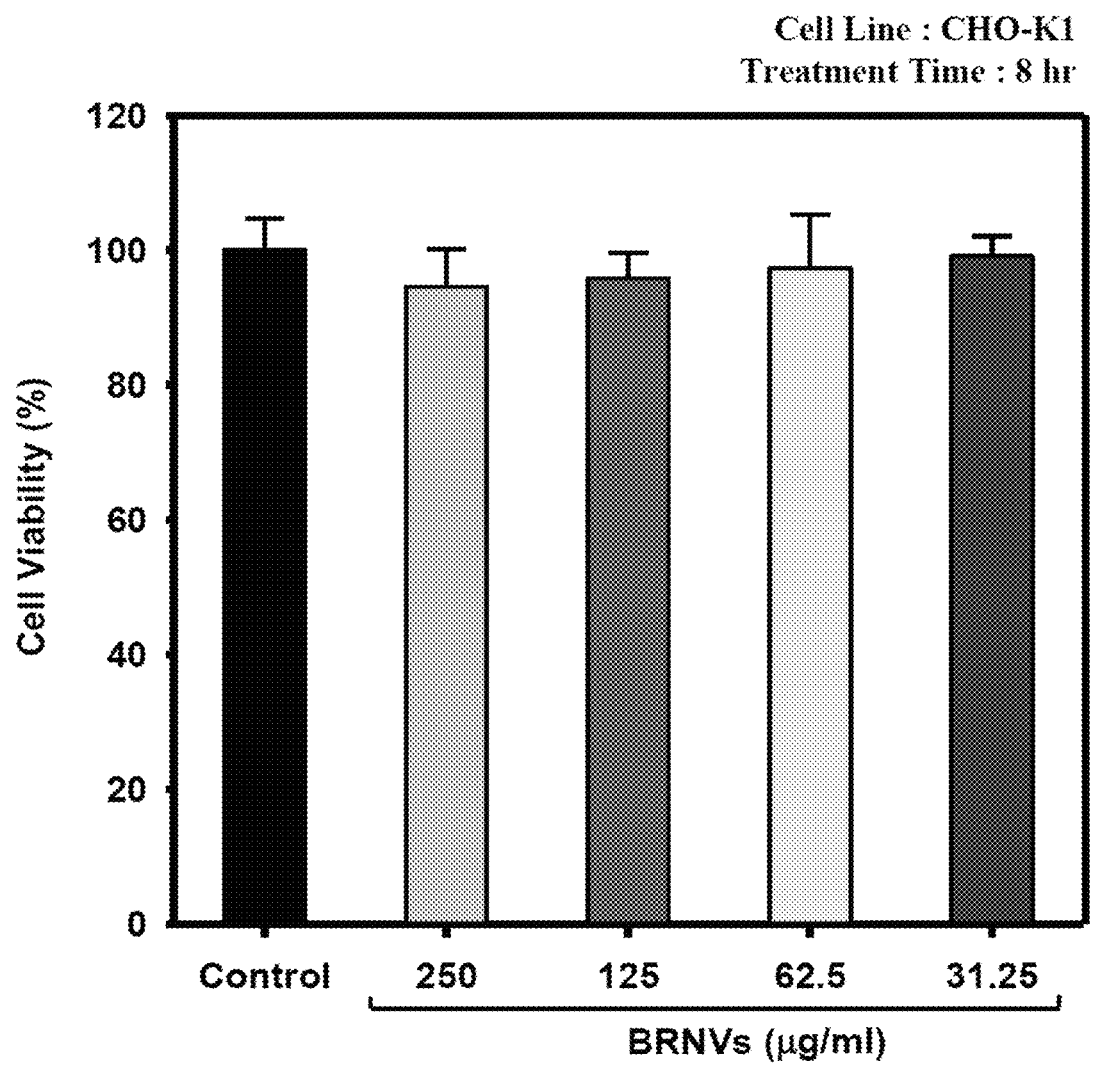
FIG. 21 shows toxicity evaluation results of bilirubin nanoparticles according to the present invention.

As shown in FIG. 21, BRNVs showed no toxicity.

Figure 22:
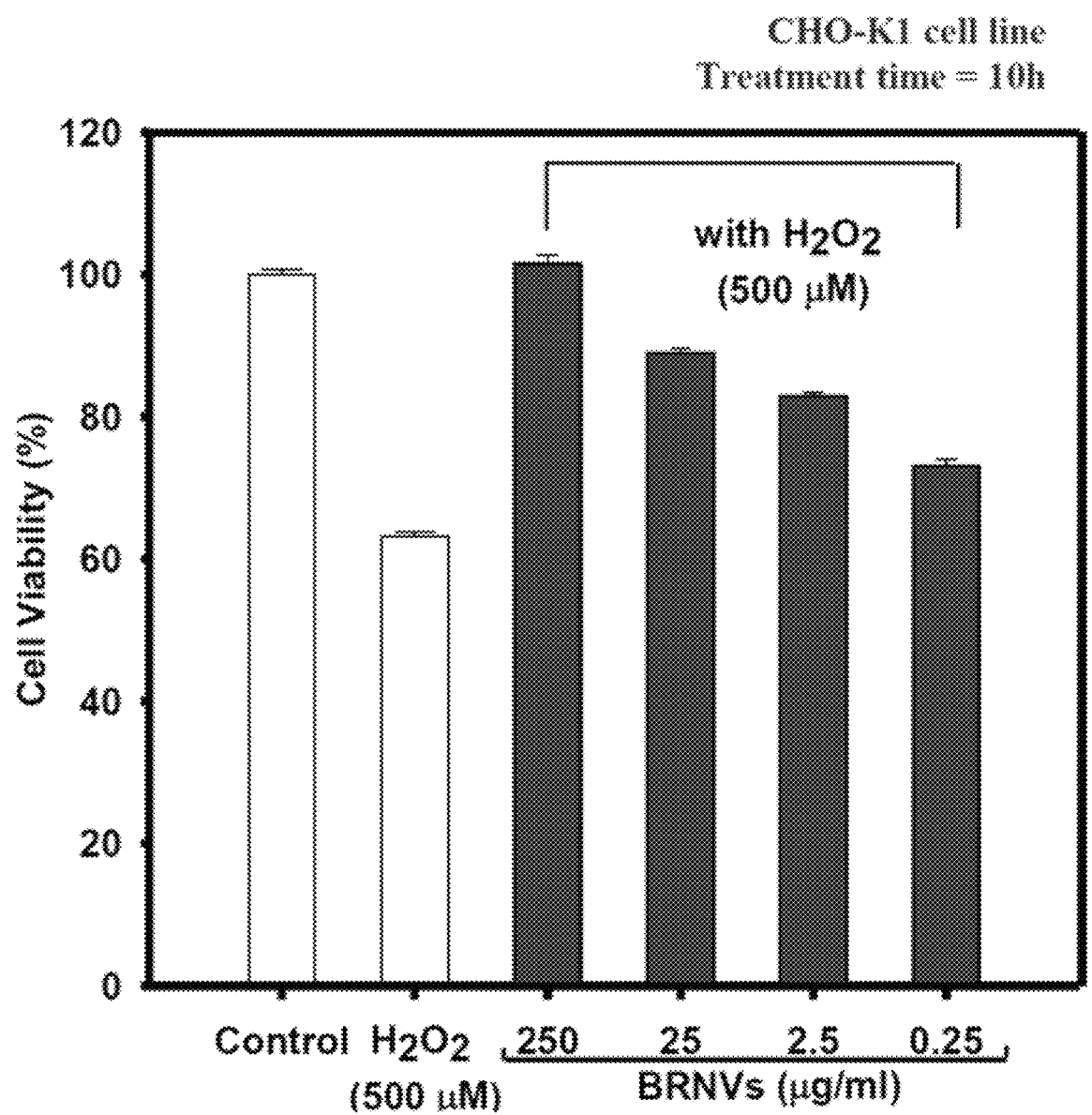
FIG. 22 is a cell viability graph showing that bilirubin nanoparticles according to the present invention can protect cells from reactive oxygen species.
Figure 23:
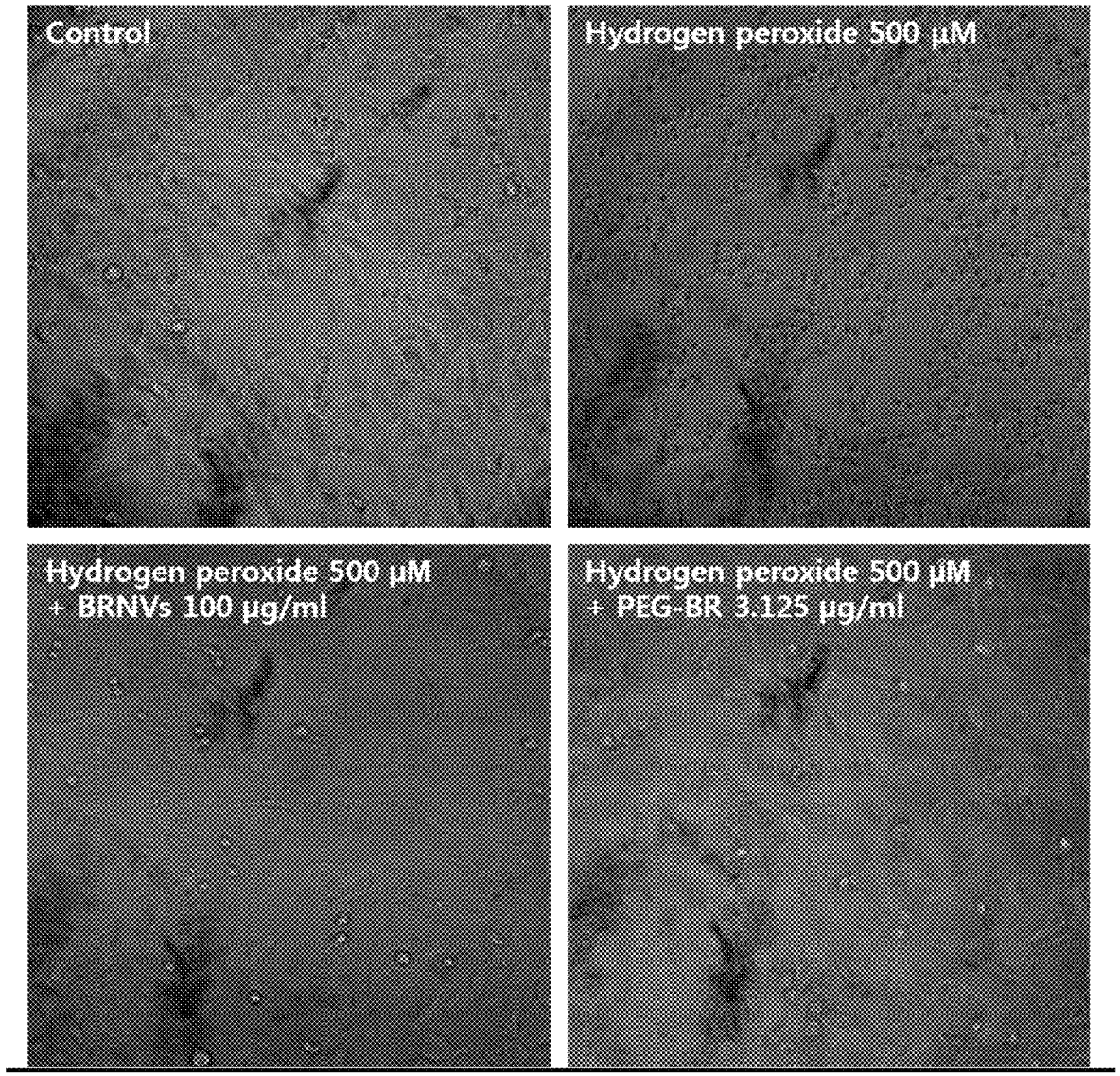
FIG. 23 illustrates cell shape images showing that bilirubin nanoparticles according to the present invention can protect cells from reactive oxygen species.
Figure 24:
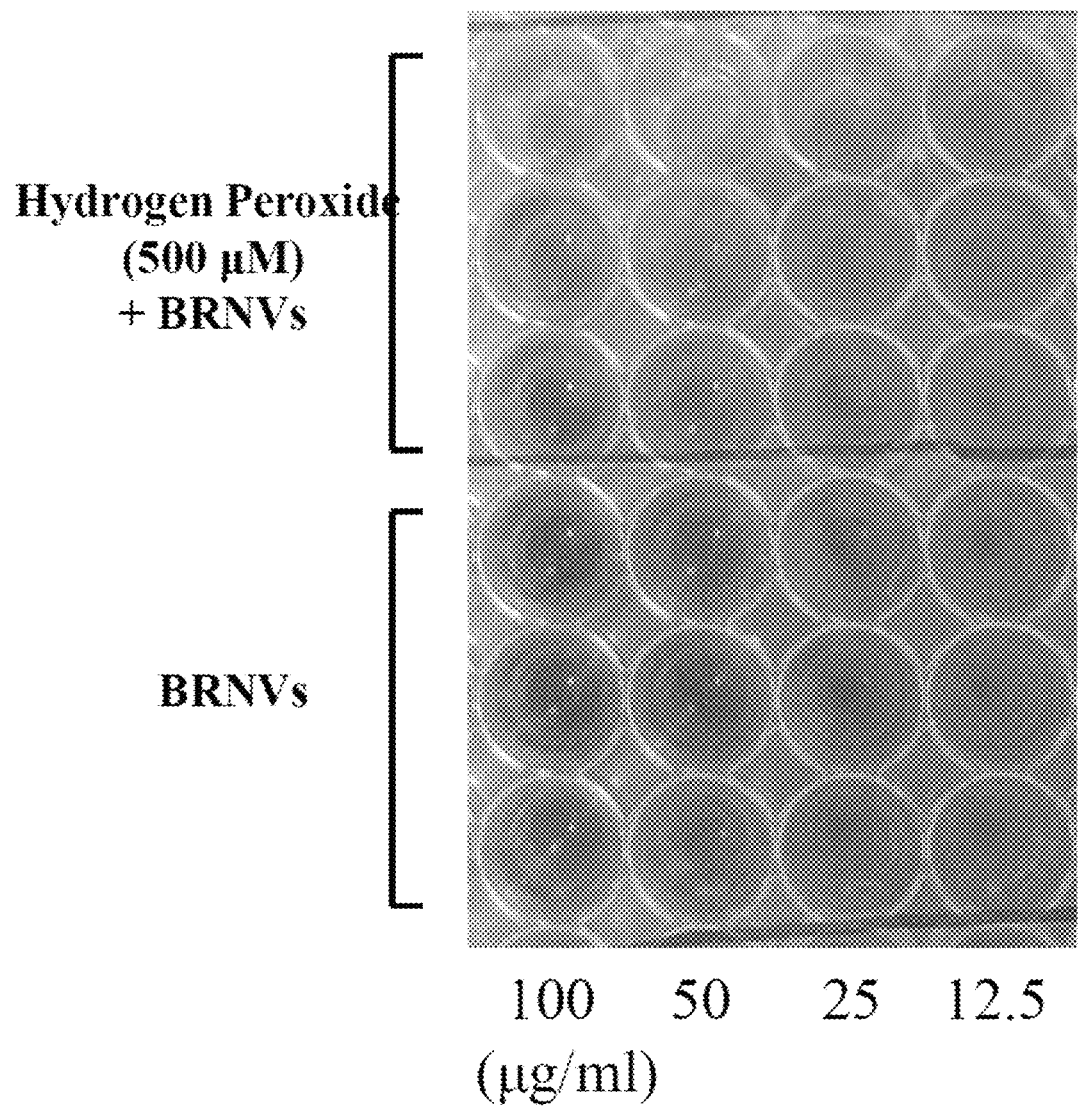
FIG. 24 shows that bilirubin nanoparticles according to the present invention are disrupted at the same time when scavenging ROS.

As shown in FIGS. 22 and 23, BRNVs effectively scavenged ROS, thereby exhibiting a cytoprotectant effect. FIG. 24 shows that the nanoparticles were disrupted together with the scavenging of ROS, through the fact that the BRNV's color became transparent when BRNVs scavenge ROS to save cells. This shows that the drug can be released if the nanoparticles involve the drug.

Figure 25A:
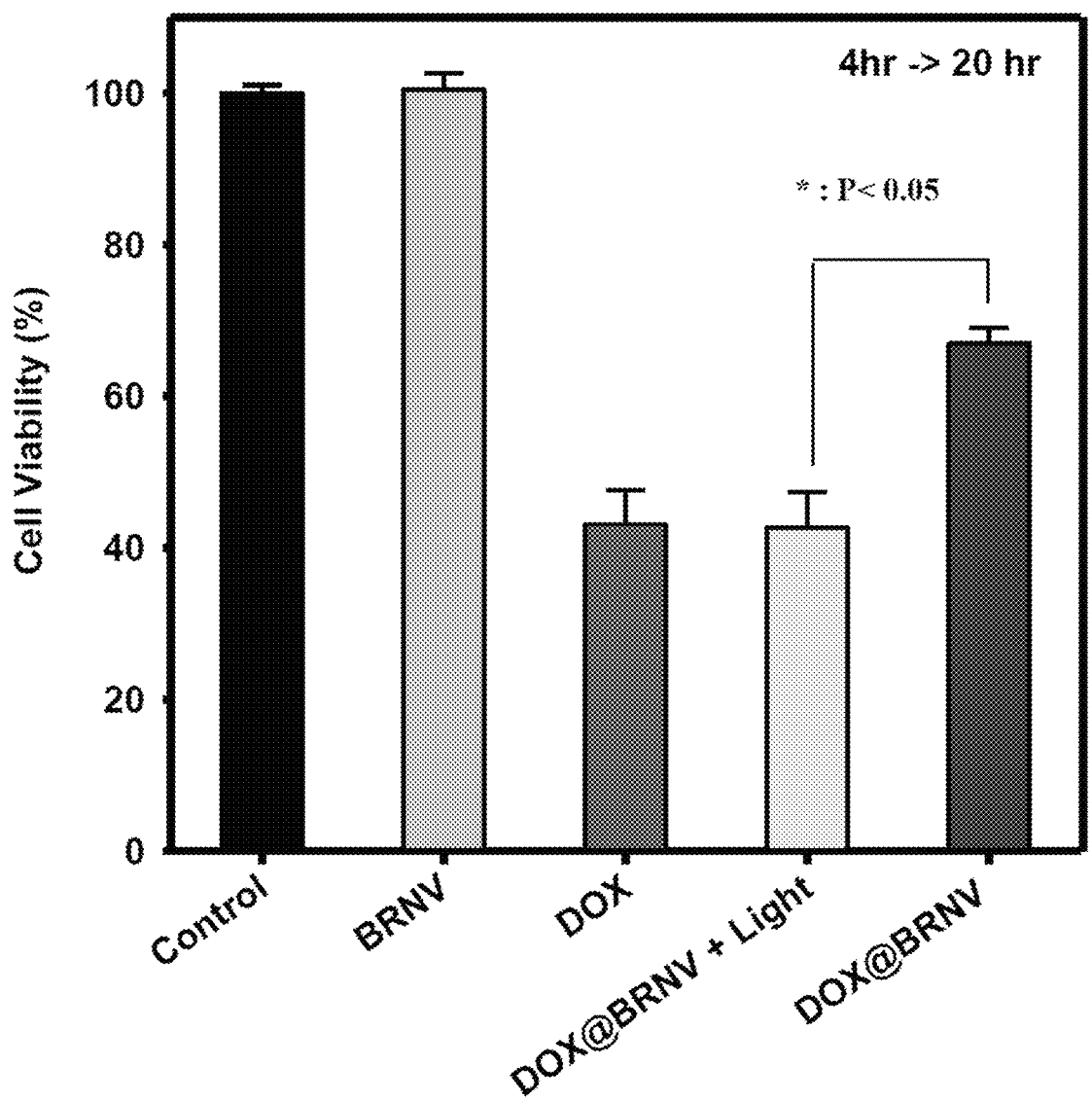
FIG. 25a shows the anticancer activity of doxorubicin-loaded bilirubin nanoparticles according to the present invention and a difference in anticancer activity depending on the presence or absence of a laser.

As shown in FIG. 25a, DOX@BRNVs showed an anticancer activity. Since DOX@BRNVs without 650 nm of laser did not lead to the effective uptake of nanoparticles per se, the delivery of the doxorubicin was slow, and thus DOX@BRNVs did not exhibit an anticancer activity as much as free DOX. However, the irradiation with 650 nm of laser for 5 min immediately after DOX@BRNVs treatment effectively released DOX, and thus DOX@BRNVs exhibited an anticancer activity as much as free DOX.

Figure 25B:
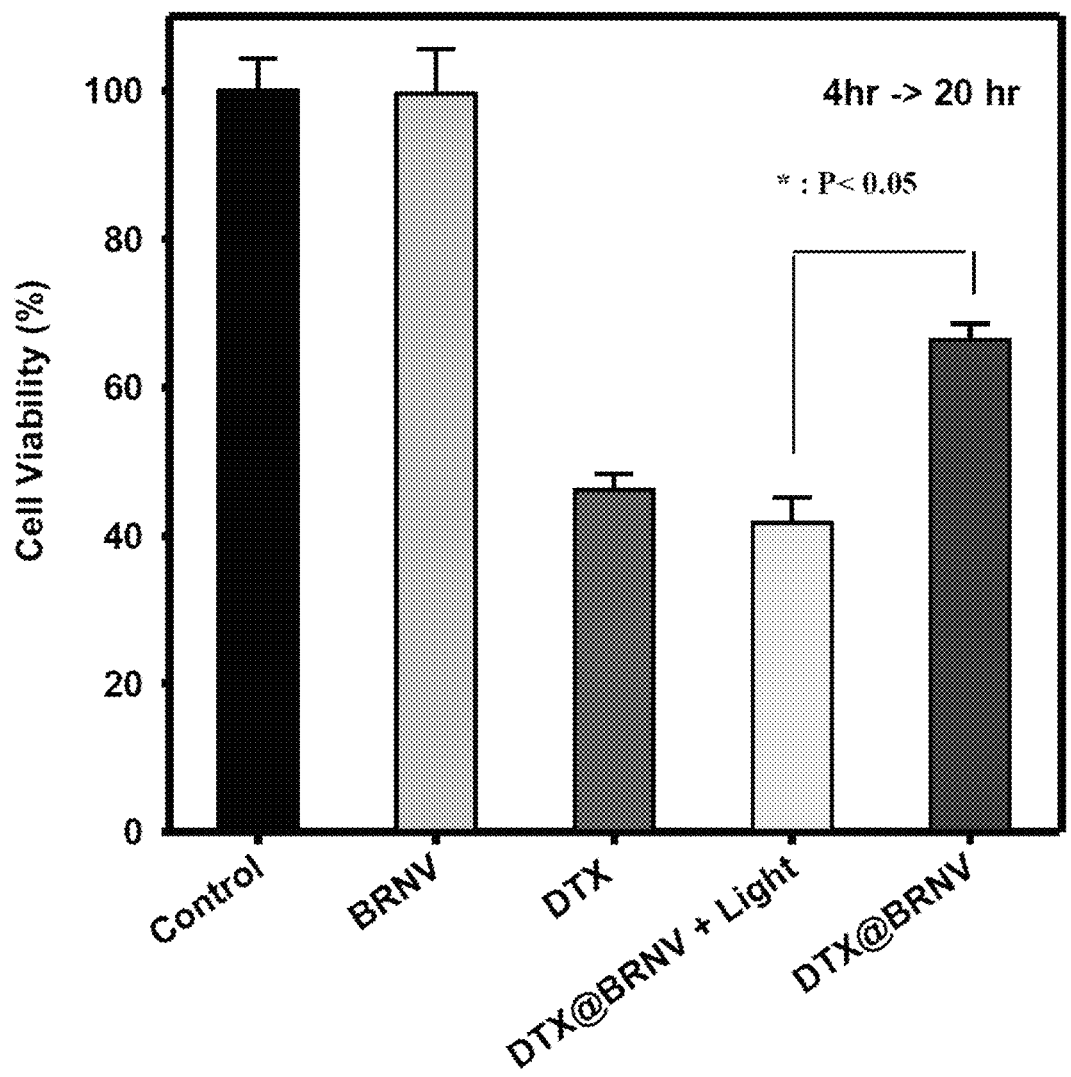
FIG. 25b shows the anticancer activity of docetaxel-loaded bilirubin nanoparticles according to the present invention and a difference in anticancer activity depending on the presence or absence of a laser.

As shown in FIG. 25b, DTX@BRNVs showed an anticancer activity. Since DTX@BRNVs without 650 nm of laser did not lead to the effective uptake of nanoparticles per se, the delivery of the docetaxel was slow, and thus DTX@BRNVs did not exhibit an anticancer activity as much as free DOX. However, the irradiation with 650 nm of laser for 5 min immediately after DTX@BRNVs treatment effectively released DTX, and thus DTX@BRNVs exhibited an anticancer activity as much as free DOX.

Anti-Angiogenic Activity of BRNVs

Figure 26:
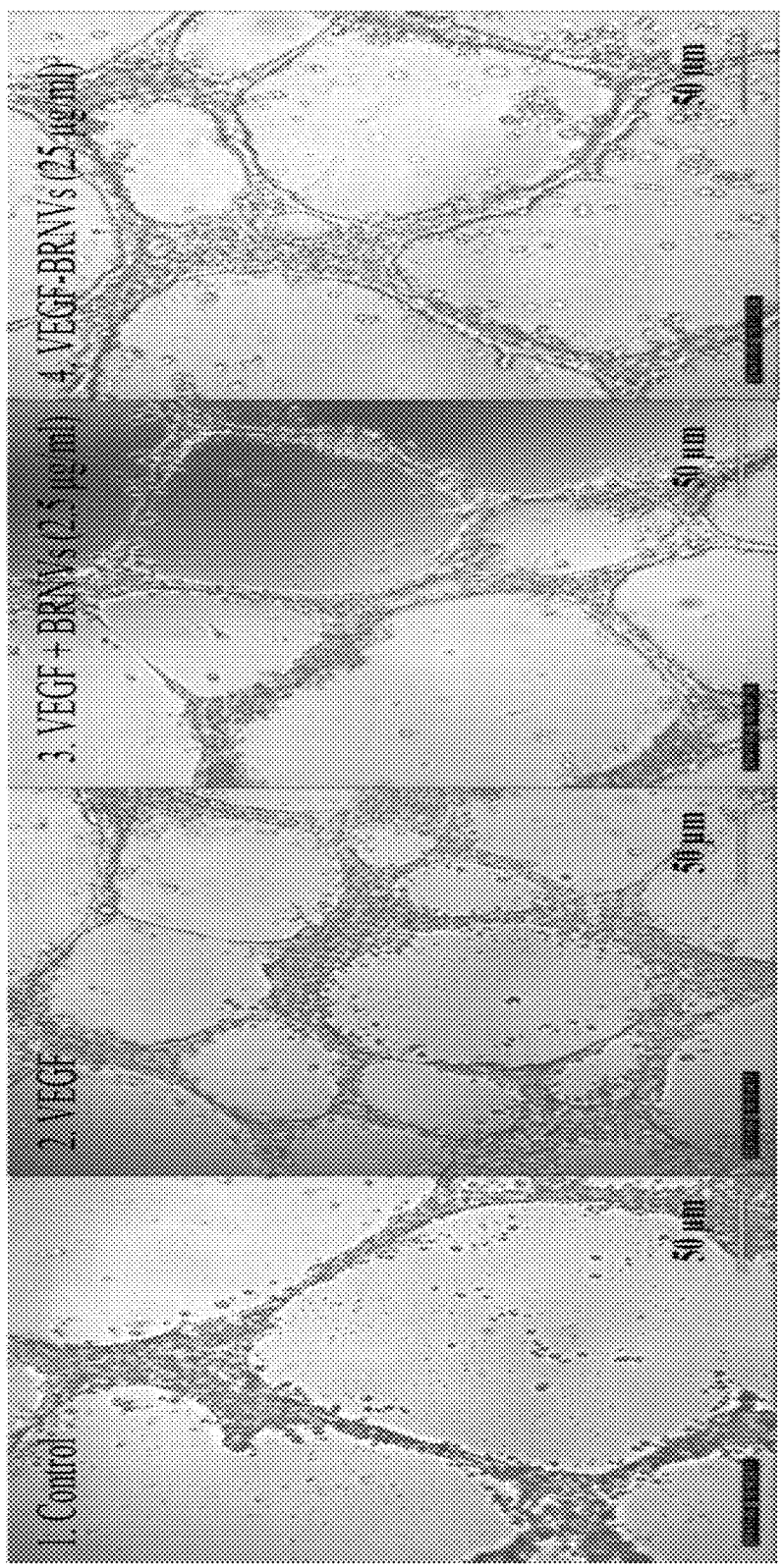
FIG. 26 shows an anti-angiogenic activity of bilirubin nanoparticles according to the present invention.

As shown in FIG. 26, the tube formation was less in the treatment with VEGF rather than the treatment with VEGF+ BRNVs, and these results show that BRNVs have an anti-angiogenic effect.

PK Profile of BRNVs

Figure 27:
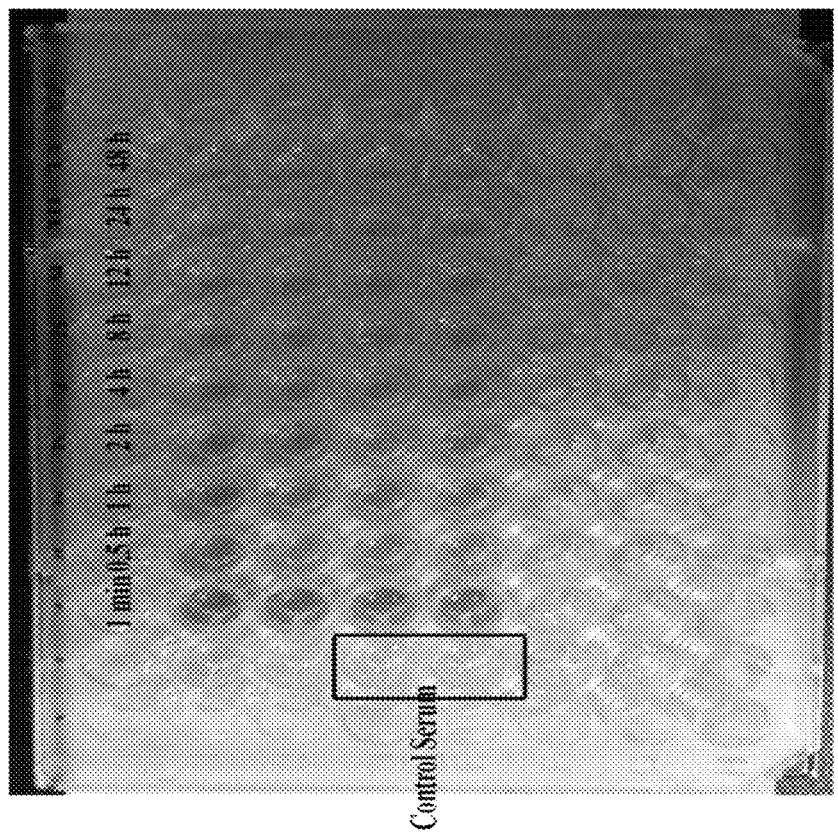
FIG. 27 shows a PK profile of bilirubin nanoparticles according to the present invention.
Figure 27:
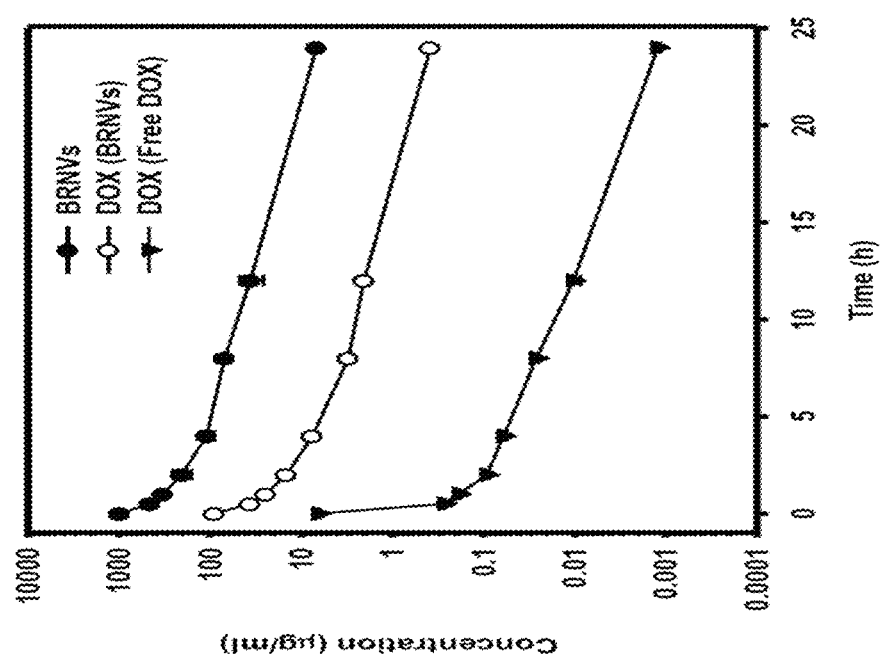

As shown in FIG. 27, DOX@BRNVs were more largely present in the blood than DOX, and thus it was verified that the nanoparticles traveled well in the blood while involving doxorubicin. In addition, as a result of investigating the pK profile of BRNVs, per se, from the absorbance at 450 nm in the blood after BRNVs were pierced, it was verified that BRNVs traveled for a long period of time.

Antiinflammatory Effect of BRNVs

Figure 28:
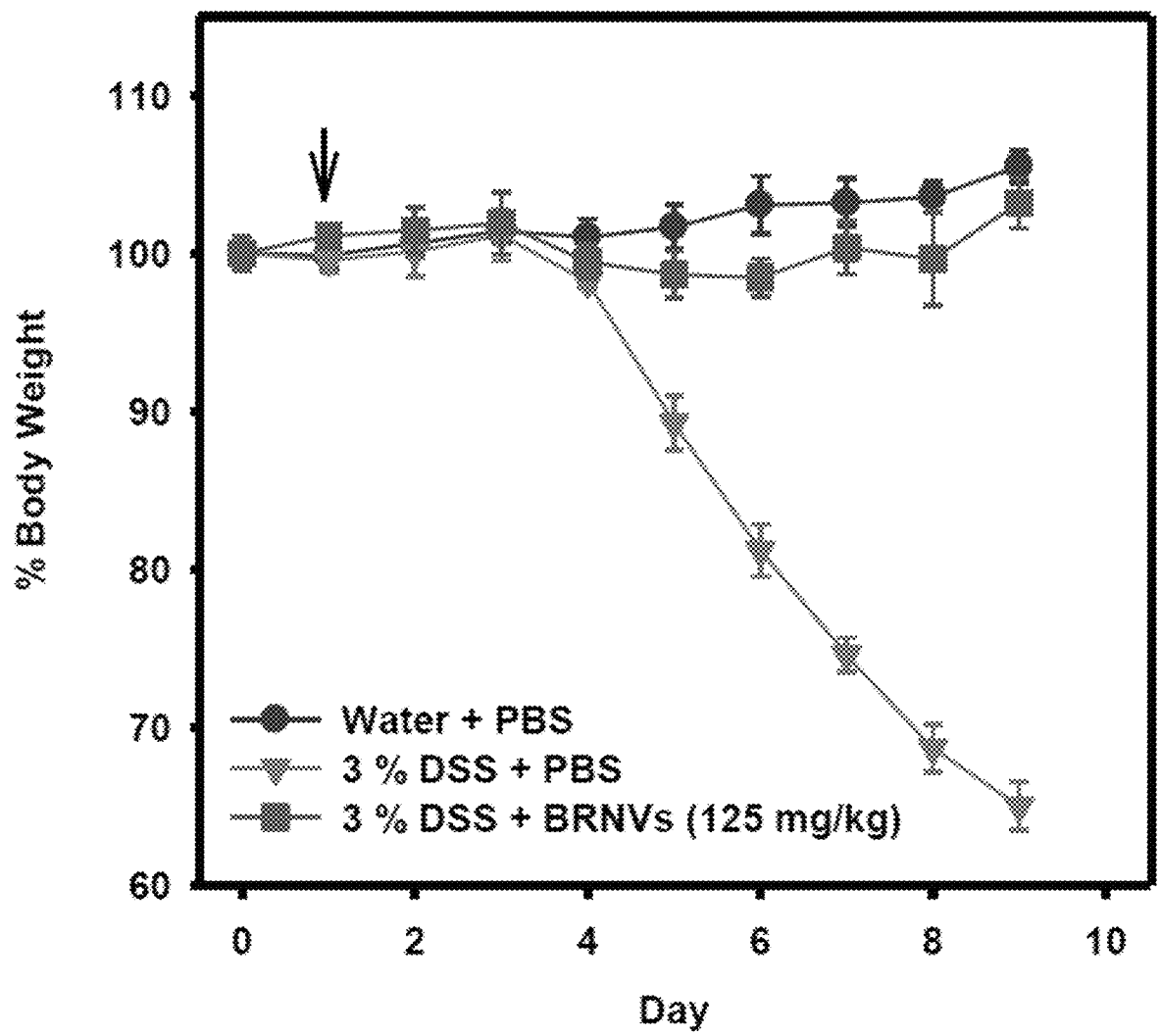
FIG. 28 illustrates a graph showing a change in body weight of a normal control group, an inflammation control group, and a bilirubin nanoparticle administration group in a test using an IBD animal model.
Figure 29:
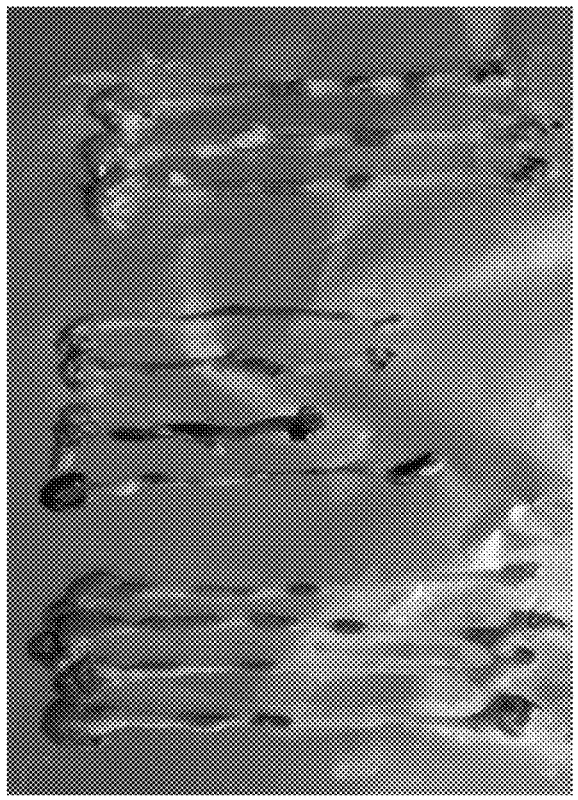
FIG. 29 illustrates an image and a graph showing the colon length of a normal control group, an inflammation control group, and a bilirubin nanoparticle administration group in a test using an IBD animal model.
Figure 29:
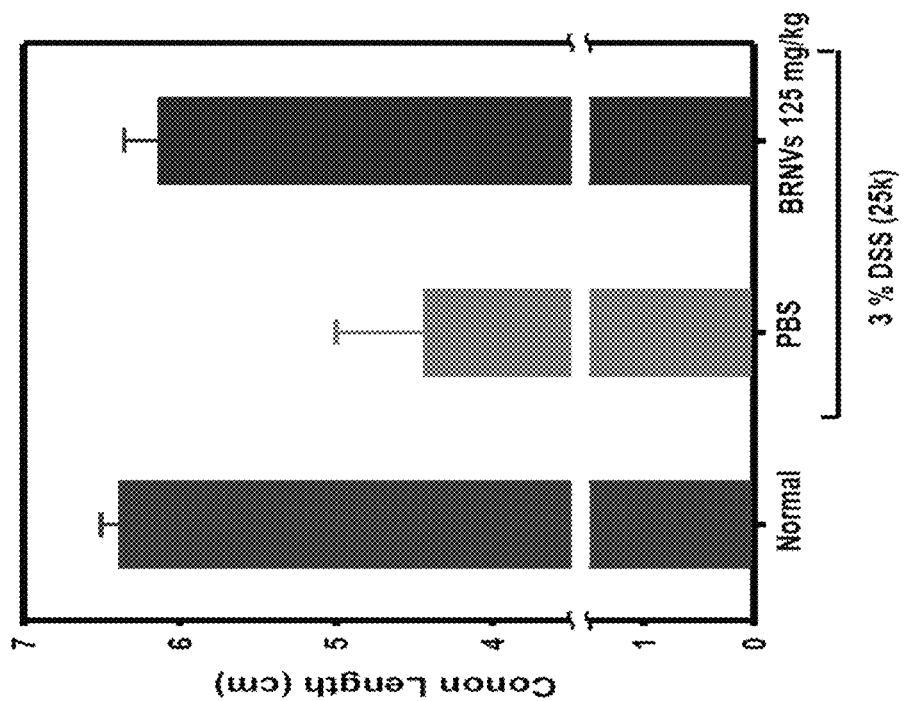
Figure 30:
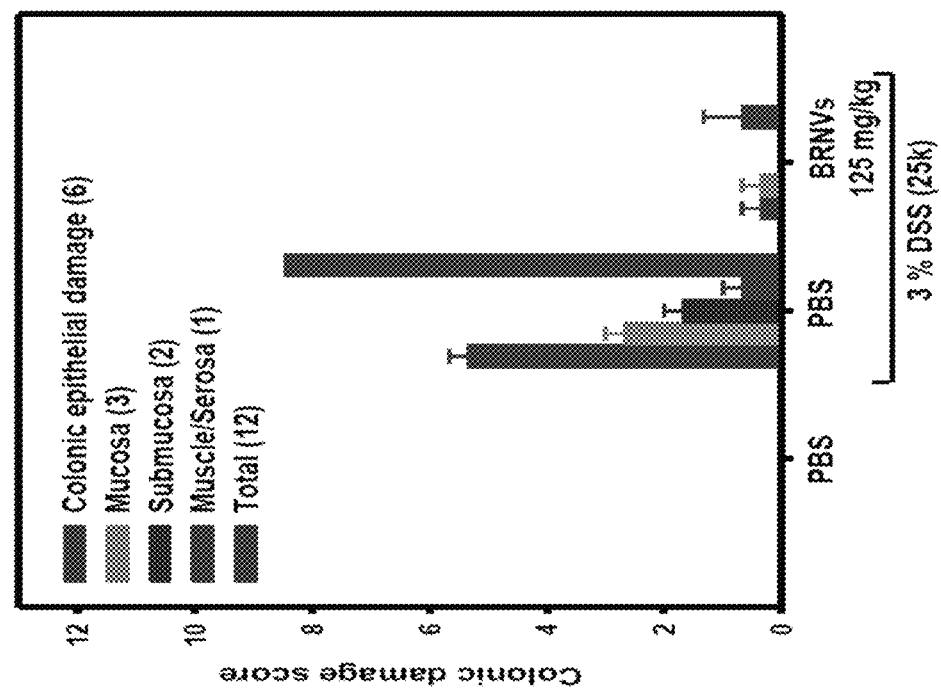
FIG. 30 illustrates a colon tissue image and an inflammation graph of a normal control group, an inflammation control group, and a bilirubin nanoparticle administration group in a test using an IBD animal model.
Figure 30:

As a result, severe body weight decrease was appeared at 5 days in inflammation control group, whereas there aren't body weight decrease during 10 days in BRNVs group as similar to healthy group (FIG. 28). Furthermore, in inflammation group colon length was short, but BRNV's colon length was normalized up to normal group (FIG. 29). As shown in H&E images of FIG. 30, in normal group, colonic epithelial's structure is well organized and it was seen may crypt in mucus layer and furthermore, there aren't immune cell infiltration in mucosa, submucosa, muscle and serosa but, in inflammation group, there are extraordinary colonic damage, ulceration and excessive immune cell infiltration into mucosa, submucosa, muscle and serosa. However, in BRNVs group, it looks like normal group (well organized mucosa layer, non immune cell infiltration). In addition, colonic damage was scored as followed method. Colonic epithelial damage score is total 6 points, and mucosa immune cell infiltration is total 3 points, submucosa immune cell infiltration 2 points, muscle/serosa 1 points (total 12 points). It was confirmed that the inflammation score of intestine tissues in BRNVs group was significantly lower that inflammation control group (FIG. 30).

Figure 31A:
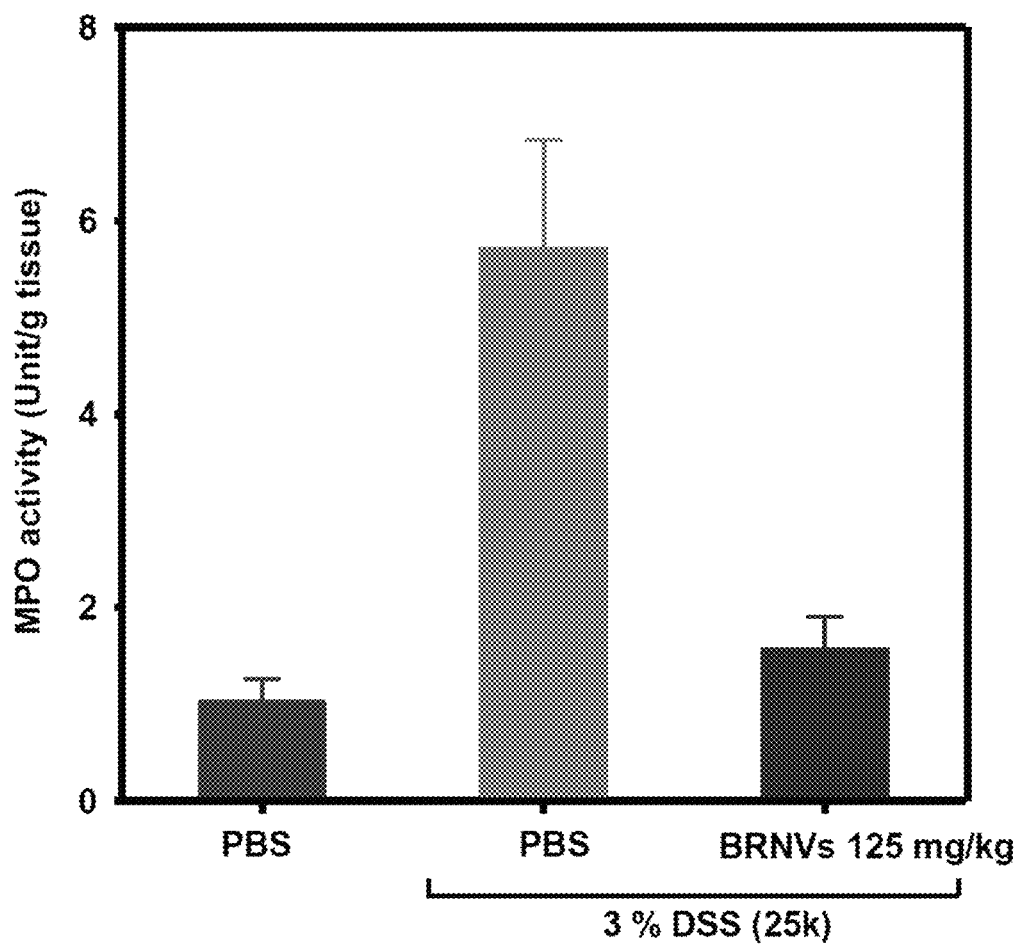
FIG. 31a illustrates a graph showing MPO activity of a normal control group, an inflammation control group, and a bilirubin nanoparticle administration group in a test using an IBD animal model.
Figure 31B:
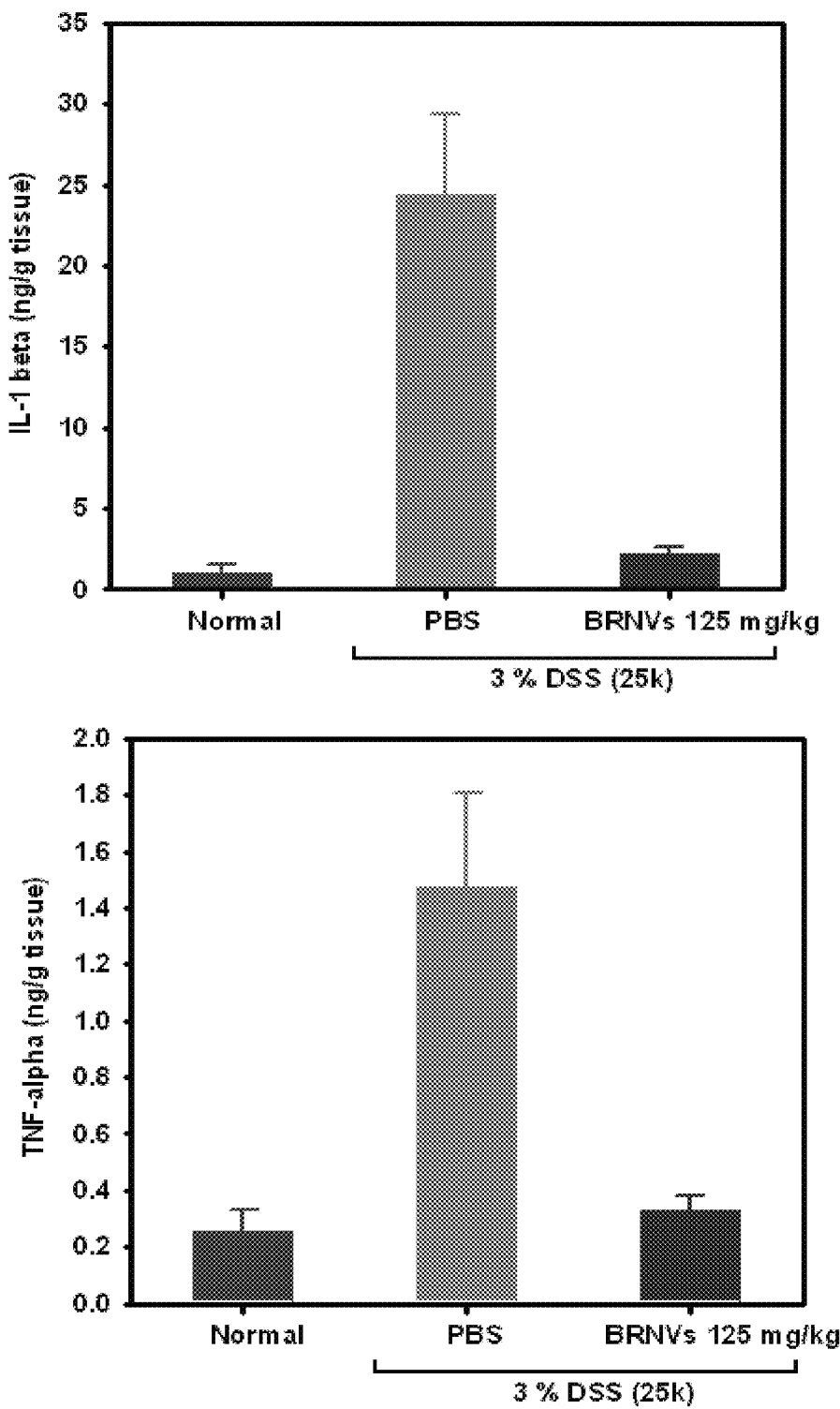
FIG. 31b and FIG. 31c illustrate graphs showing the levels of pro-inflammatory cytokines of a normal control group, an inflammation control group, and a bilirubin nanoparticle administration group in a test using an IBD animal model.
Figure 31C:
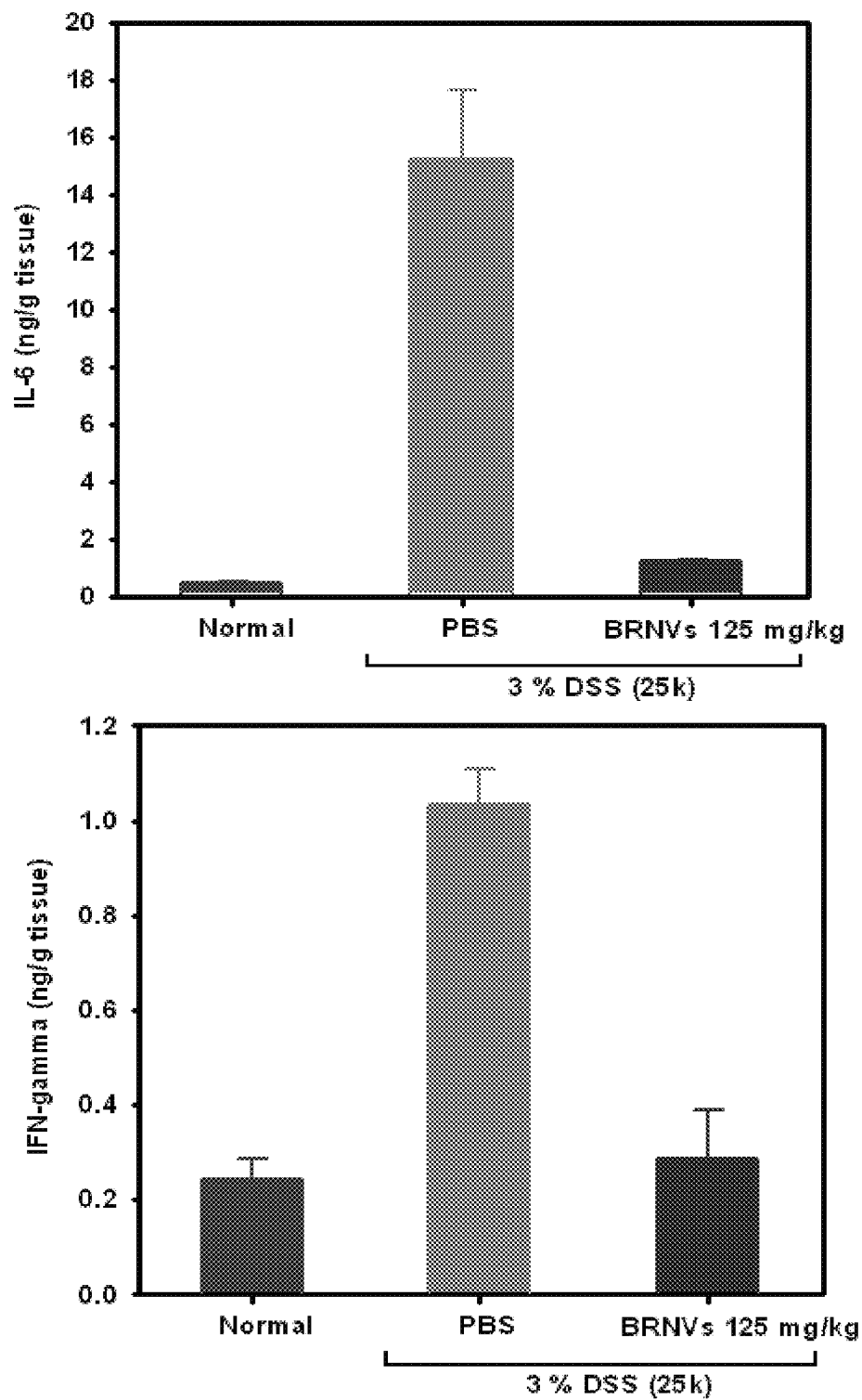

MPO activity and cytokine associated with inflammation was also assessed. As a result, in BRNVs group, MPO activity and II-1 beta, IL-6 TNF-alpha IFN-gamma's levels were normalized like normal tissues, whereas these of inflammation control group were high (FIGS. 31a-31c).

These results prove that BRNVs can protect against DSS induced colitis.

Inflammation Site Targeting Ability of BRNVs

Four possibilities could be seen from the fluorescence value of ICG. The first possibility is the uptake of nanoparticles, per se, into the liver. The second possibility is that ICG is released from nanoparticles to the liver while traveling in the blood, considering that ICG is mainly excreted into the liver when ICG is injected into the blood. The third possibility is that inflammation occurs by DSS in the liver. The fourth possibility is that ICG-loaded nanoparticles arrive at the inflammation site of the colon through capillary vessels of the leaky colon, and here, ICG is fast released by ROS to be present in the submucous layer of the colon, and the ICG again arrives at the liver through the hepatic portal vein and then is released in the liver.

Figure 32A:
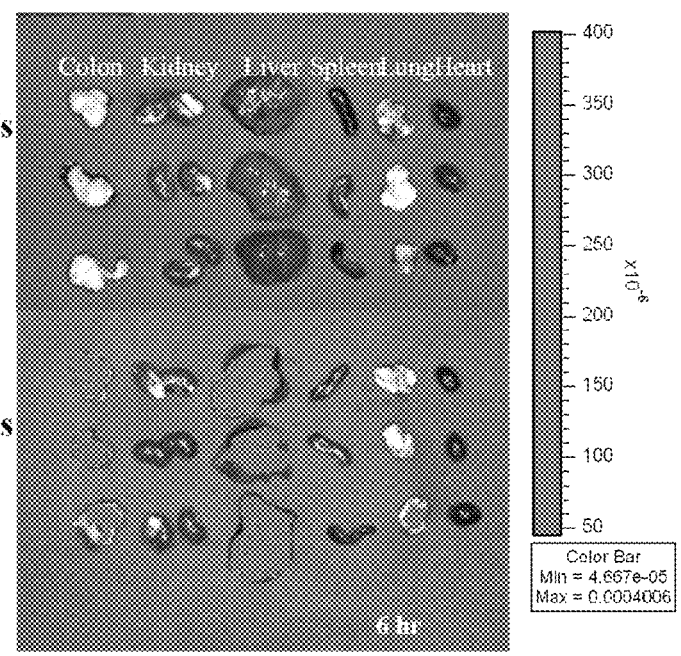
FIG. 32a shows that an animal model without inflammation had a lower fluorescence value in the liver than an IBD animal model. In addition, the image shows that bilirubin nanoparticles are selectively accumulated in the IBD inflammation and then ICG is released by ROS.
Figure 32B:
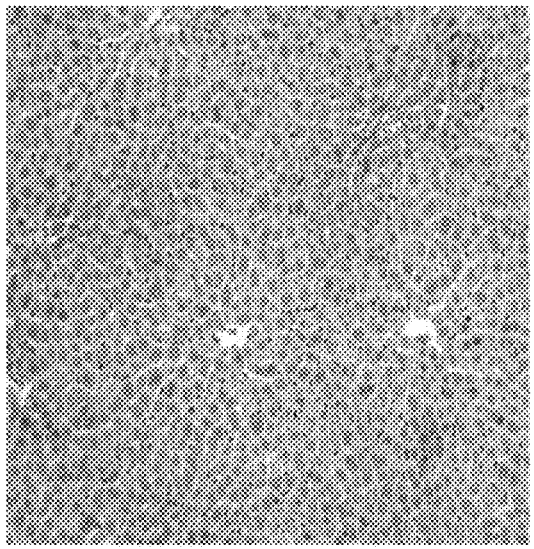
FIG. 32b shows liver H&E images of an IBD animal model and a normal group.
Figure 32B:
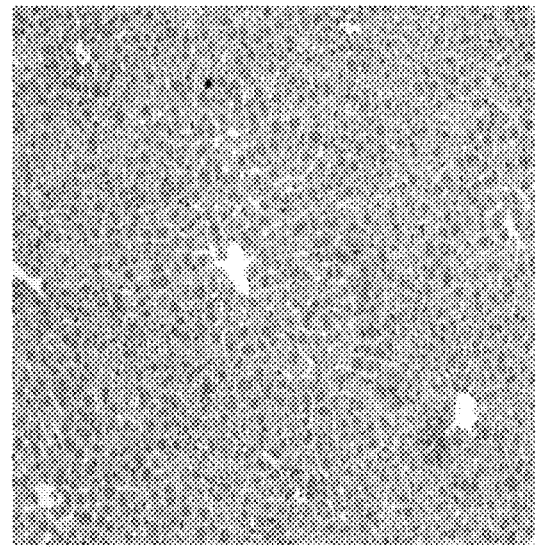

The first and second possibilities are not theoretically correct since a low fluorescence value is observed in the liver of an animal model without inflammation (FIG. 32a). The third possibility is not correct since, as shown in the H&E image, inflammation did not occur in the liver in the DSS inflammation animal model (FIG. 32b). Hence, it is preferable to construe using the fourth possibility. That is, the present test results show that BRNVs selectively arrive at the inflammation tissue, and then releases ICG by ROS.

Anticancer Activity of BRNVs

Figure 33:
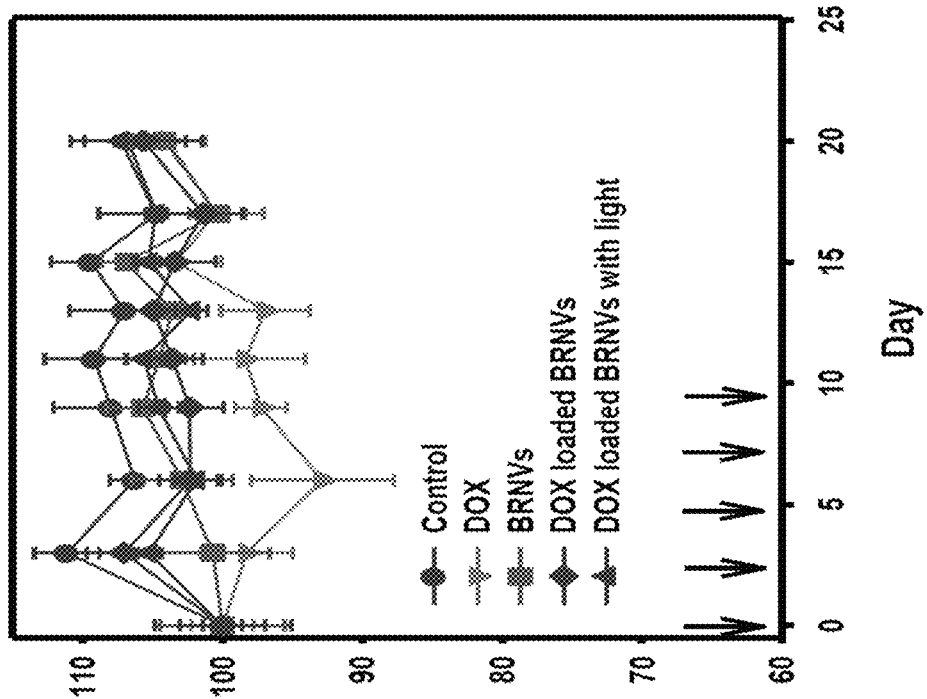
FIG. 33 shows anticancer activities of bilirubin nanoparticles and the doxorubicin-loaded bilirubin nanoparticles according to the present invention.
Figure 33:
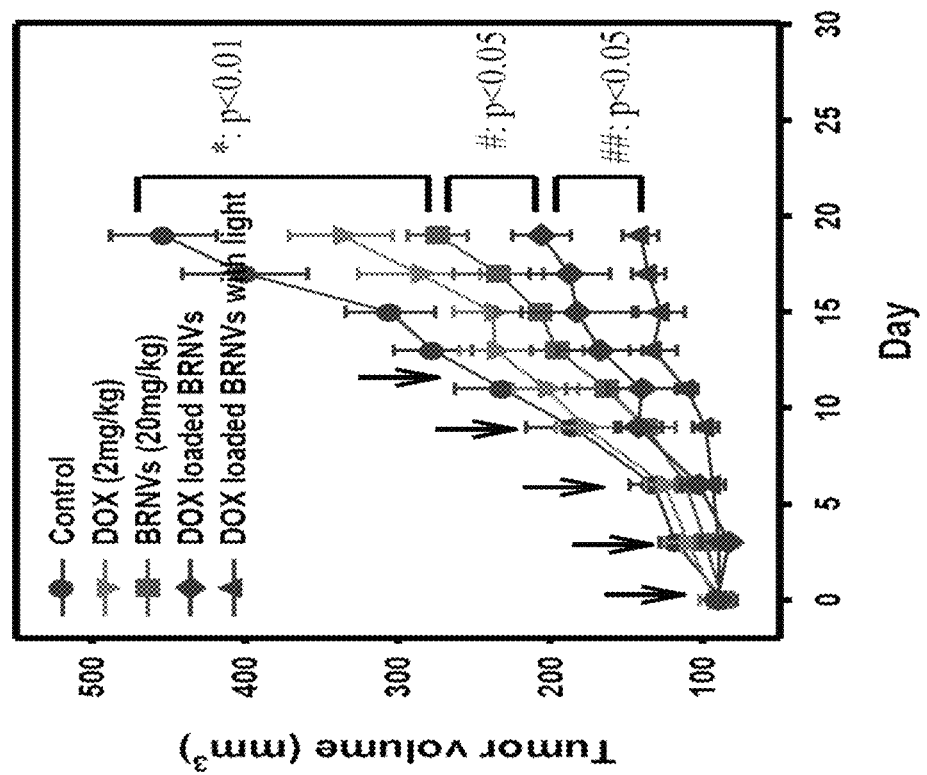

It can be seen from the results of FIG. 33 that doxorubicin-loaded or -unloaded nanoparticles had more excellent efficacy in the anticancer ability than free doxorubicin. In addition, it could be observed that the group of DOX@BRNVs with the laser statistically significantly further inhibited cancer growth than the group of DOX@BRNVs without the laser. The nanoparticles remain in the blood, and then arrive at the cancer tissue by EPR effects, and all the nanoparticles do not remain to release the drug, but only some of the nanoparticles remain in the cancer tissue and the other nanoparticles again escape along the fast blood current. Here, the nanoparticles release the drug by the irradiation of the laser before the nanoparticles again promptly escape into the blood, thereby allowing the delivery of doxorubicin with a significant higher concentration to the cancer tissue. Through this, it is supposed that the irradiation of the laser would produce a more effective anticancer ability. Moreover, interesting results could be obtained that only BRNVs, per se, had an anticancer activity, and this is determined to be due to the anti-angiogenic activity resulting from the scavenging of ROS.

Toxicity Evaluation of BRNVs

Figure 34:
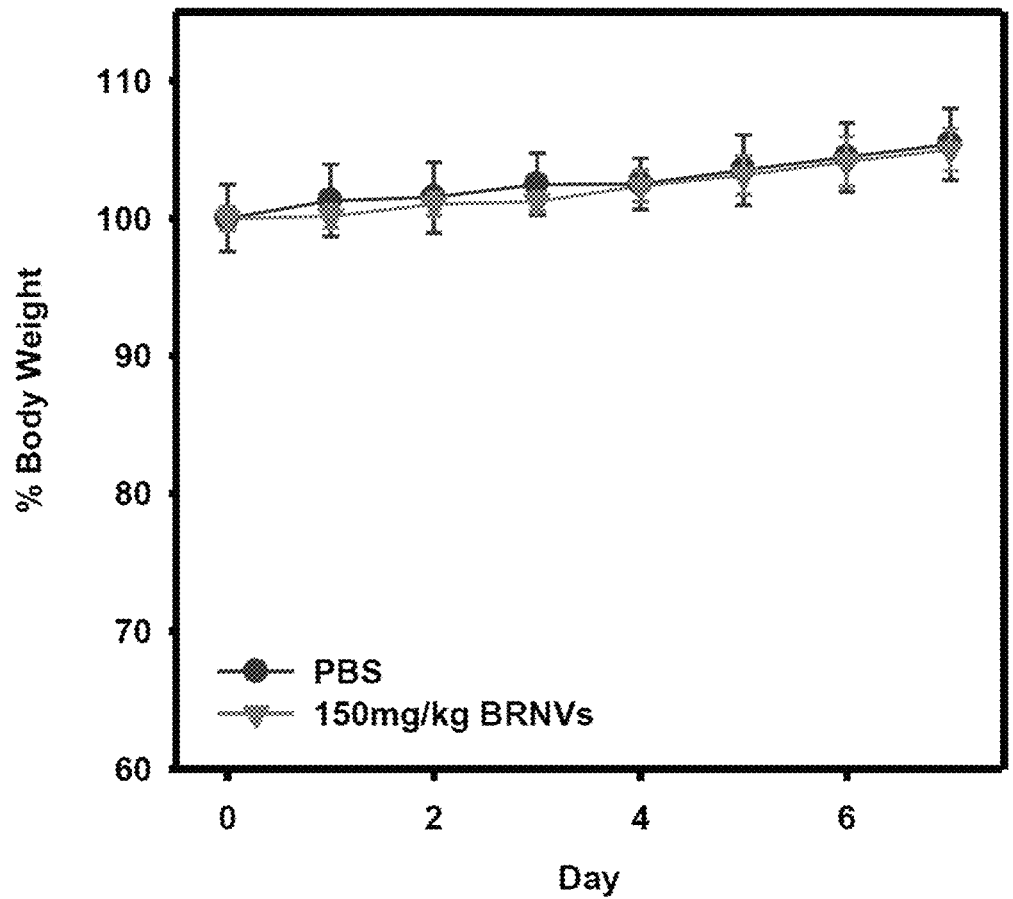
FIG. 34 shows a change in body weight by the administration of bilirubin nanoparticles according to the present invention.
Figure 35:
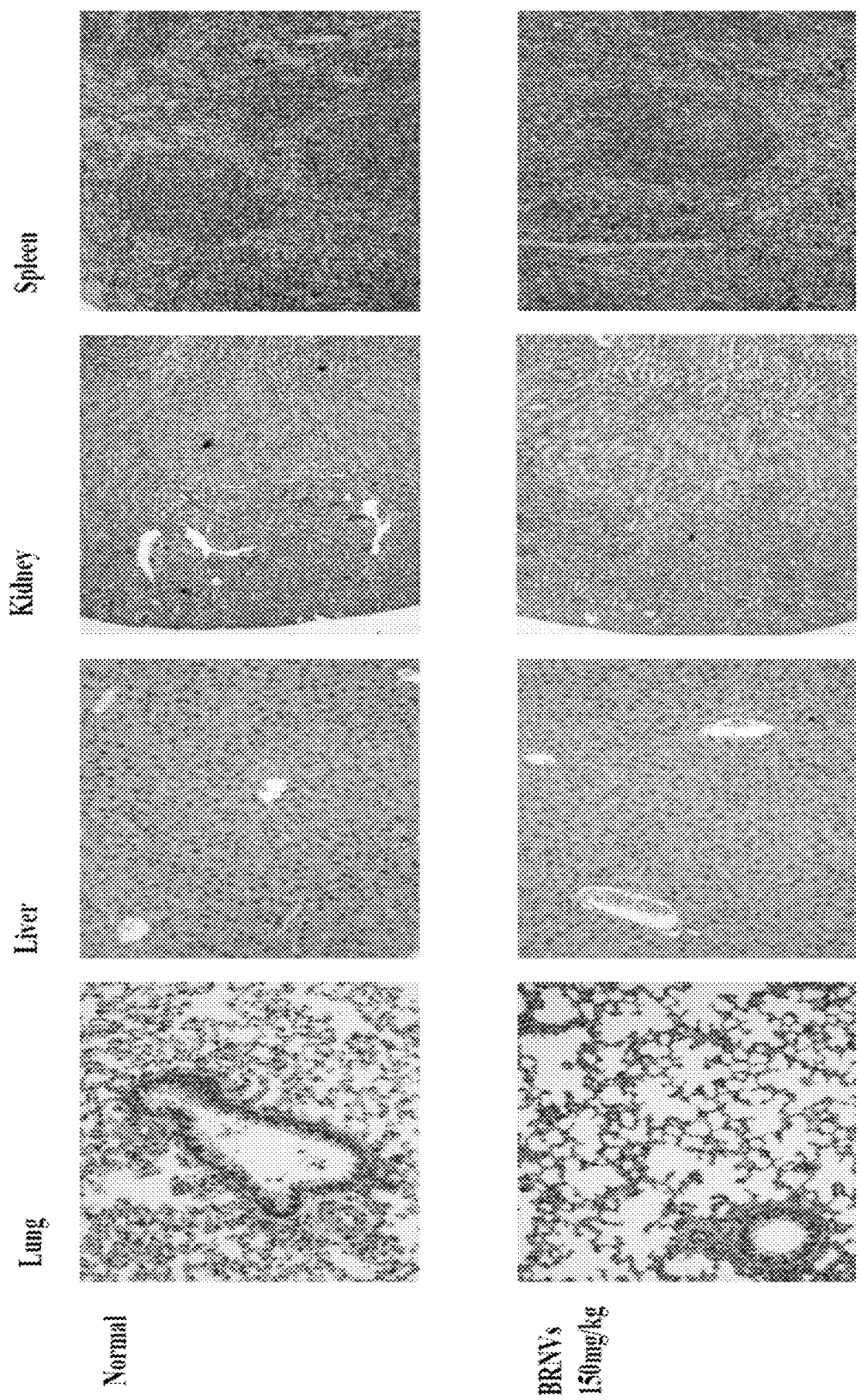
FIG. 35 shows H&E images of major organs by the administration of bilirubin nanoparticles according to the present invention.

As shown in FIG. 34, no severe change in the body weight was not shown for 7 days after high-volume of nanoparticles were injected. After 7 days, major organs were extracted, and then H&E imaging was performed. As a result, as shown in FIG. 35, no distinctive inflammation indication was observed. This established that BRNVs was safe in the body.

EPR effect of BRNVs

Figure 36:
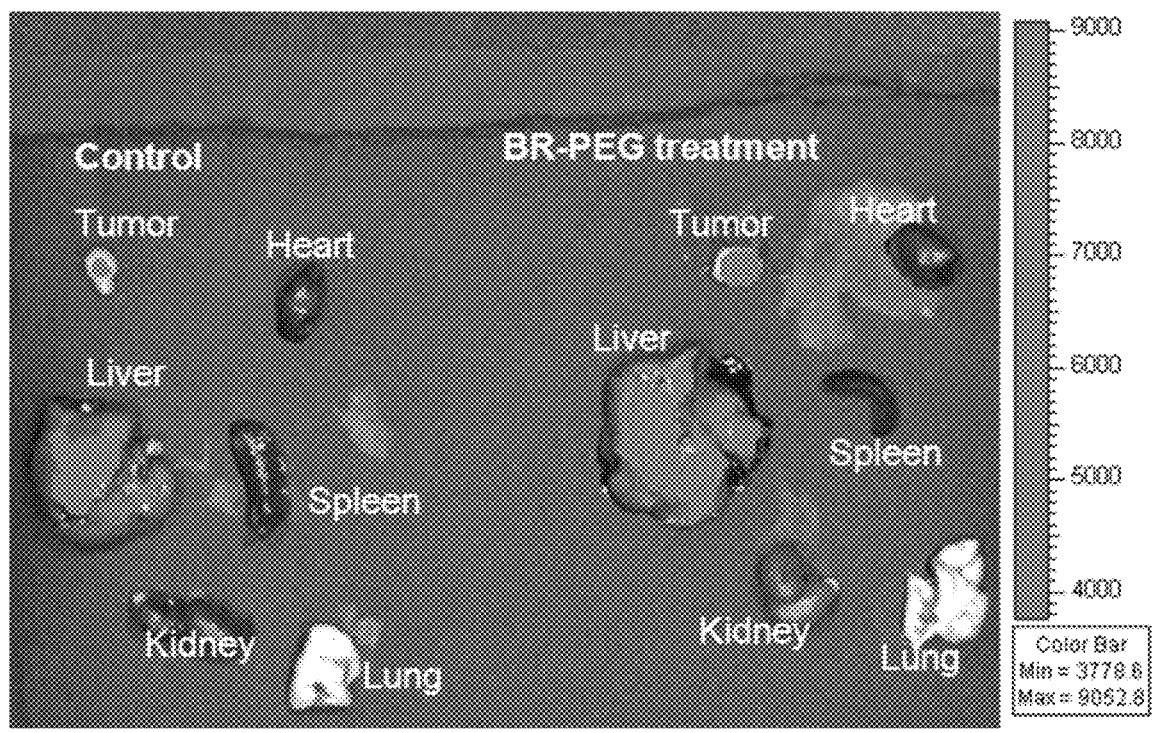
FIG. 36 shows that bilirubin nanoparticles were selectively accumulated in the tumor tissue.

The ability of PEG-BR to be localized to tumor tissue by EPR effect due to interatctions between nanoparticle's physicochemical properties and the anatomy and physiology of the tumor environment was examined. As shown in FIG. 36, BRNVs treatment group's fluorescence intensity in tumor tissue was much stronger compared to the control group. These results show that BRNVs can accumulate into tumor tissue selectively.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A bilirubin nanoparticle comprising a plurality of a composite comprising bilirubin and a hydrophilic polymer;
   wherein the hydrophilic polymer is covalently bound to a carboxyl group of the bilirubin;
   the hydrophilic polymer is selected from the group consisting of polyethyleneglycol (PEG), poly(acrylic acid), poly(acrylate), poly(acrylamide), poly(vinylalcohol), polyoxide, cellulose, starch, polysaccharides, polyelectrolyte, poly(l-nitropropylene), poly(N-vinyl pyrrolidone), poly(vinyl amine), poly(betahydroxyethyl methacrylate), polyethyleneoxide, poly(ethylene oxide-b-propylene oxide), and polylysine; or
   the hydrophilic polymer is selected from the group consisting of collagen, chitosan, gelatin, acacia gum, dextran, fibrin, hyaluronic acid, pectin, agar, galactomannan, xanthan, and alginate; or
   the hydrophilic polymer is a peptide comprising two or more amino acids.

2. The bilirubin nanoparticle of claim 1, wherein the bilirubin nanoparticle is in the form of a micelle.

3. The bilirubin nanoparticle of claim 1, further comprising a cargo;
wherein the bilirubin nanoparticle encapsulates the cargo.

4. The bilirubin nanoparticle of claim 1, wherein the hydrophilic polymer comprises an amine group at a side chain or a terminus; and the amine group is covalently bound to the carboxyl group to form an amide.

5. The bilirubin nanoparticle of claim 3, wherein the cargo is an anti-cancer agent.

6. A method of treating an inflammatory disease, comprising administering to a subject in need thereof an effective amount of the bilirubin nanoparticle of claim 3;
wherein the cargo is an anti-inflammatory agent.

7. The method of claim 6, further comprising subsequently administering an effective amount of photo-stimulation to the subject.

8. A method of treating an angiogenesis-related disease, comprising administering to a subject in need thereof an effective amount of the bilirubin nanoparticle of claim 3;
wherein the cargo is an anti-angiogenic inhibitor.

9. A method of decreasing reactive oxygen species, comprising administering to a subject in need thereof an effective amount of a composition comprising the bilirubin nanoparticle of claim 1.

10. The bilirubin nanoparticle of claim 1, wherein the hydrophilic polymer is selected from the group consisting of polyethyleneglycol (PEG), poly(acrylic acid), poly(acrylate), poly(acrylamide), poly(vinylalcohol), polyoxide, cellulose, starch, polysaccharides, polyelectrolyte, poly(-nitropropylene), poly(N-vinyl pyrrolidone), poly(vinyl amine), poly(betahydroxyethyl methacrylate), polyethyleneoxide, poly(ethylene oxide-b-propylene oxide), and polylysine.

11. The bilirubin nanoparticle of claim 10, wherein the hydrophilic polymer is polyethyleneglycol (PEG).

12. The bilirubin nanoparticle of claim 1, wherein the hydrophilic polymer is selected from the group consisting of collagen, chitosan, gelatin, acacia gum, dextran, fibrin, hyaluronic acid, pectin, agar, galactomannan, xanthan, and alginate.

13. The bilirubin nanoparticle of claim 12, wherein the hydrophilic polymer is chitosan.

14. The bilirubin nanoparticle of claim 12, wherein the hydrophilic polymer is hyaluronic acid.

15. The bilirubin nanoparticle of claim 1, wherein the hydrophilic polymer is a peptide comprising two or more amino acids.

16. The bilirubin nanoparticle of claim 1, wherein the hydrophilic polymer comprises a hydroxyl group at a side chain or a terminus; and the hydroxyl group is covalently bound to the carboxyl group to form an ester.

* * * * *